US012601803B2

(12) United States Patent
Abel et al.

(10) Patent No.: US 12,601,803 B2
(45) Date of Patent: Apr. 14, 2026

(54) SYSTEM FOR MACHINE LEARNING-BASED MODEL TRAINING AND PREDICTION FOR EVALUATION OF PAIN

(71) Applicant: ACLARION, INC., San Mateo, CA (US)

(72) Inventors: James Charles Abel, Emerald Hills, CA (US); James Clayton Peacock, III, San Carlos, CA (US); Ricardo Dario Pradenas, Irvine, CA (US)

(73) Assignee: Aclarion, Inc., San Mateo, CA (US)

( * ) Notice: Subject to any disclaimer, the term of this patent is extended or adjusted under 35 U.S.C. 154(b) by 478 days.

(21) Appl. No.: 18/050,841

(22) Filed: Oct. 28, 2022

(65) Prior Publication Data

US 2023/0140742 A1     May 4, 2023

Related U.S. Application Data

(60) Provisional application No. 63/263,321, filed on Oct. 29, 2021.

(51) Int. Cl.
*G01R 33/485* (2006.01)
*G01R 33/48* (2006.01)
*G16H 50/20* (2018.01)

(52) U.S. Cl.
CPC ....... *G01R 33/485* (2013.01); *G01R 33/4828* (2013.01); *G16H 50/20* (2018.01)

(58) Field of Classification Search
CPC .............. G01R 33/485; G01R 33/4828; G01R 33/5608; G01R 33/465; G01R 33/4625; G16H 50/20; G16H 20/40; G16H 50/50; G16H 50/70; A61B 5/4566; A61B 5/055
See application file for complete search history.

(56) References Cited

U.S. PATENT DOCUMENTS

| | | | |
|---|---|---|---|
| 2010/0329529 A1 | 12/2010 | Feldman et al. | |
| 2014/0064586 A1* | 3/2014 | Peacock, III | A61B 5/055 |
| | | | 382/131 |
| 2014/0156573 A1* | 6/2014 | Szyperski | G01R 33/465 |
| | | | 706/12 |
| 2018/0329009 A1* | 11/2018 | James | A61B 5/7203 |
| 2019/0287674 A1 | 9/2019 | Nitta et al. | |
| 2020/0178889 A1* | 6/2020 | Mountford | A61B 5/7264 |
| 2020/0408863 A1* | 12/2020 | Liang | G01R 33/5615 |
| 2022/0117552 A1* | 4/2022 | Kim | A61B 5/055 |

FOREIGN PATENT DOCUMENTS

| | | |
|---|---|---|
| KR | 10-2021-0055897 A | 5/2021 |
| WO | WO 2020/106896 A1 | 5/2020 |
| WO | WO 2021/108043 A1 | 6/2021 |

OTHER PUBLICATIONS

International Search Report and Written Opinion dated Mar. 2, 2023 in PCT Application No. PCT/US2022/048232 in 8 pages.

* cited by examiner

*Primary Examiner* — Baisakhi Roy
(74) *Attorney, Agent, or Firm* — Knobbe, Martens, Olson & Bear, LLP

(57) ABSTRACT

Systems and methods are provided for using machine learning (ML) models to evaluate data generated during MRI procedures, such as magnetic resonance spectroscopy (MRS) data, to evaluate patient disc pain. An ML-based disc assessment system can evaluate MRS spectrum data ML models trained to classify the MRS spectrum based on diagnostic and/or outcome-based ground truth data.

22 Claims, 9 Drawing Sheets

TRAINING AN ML-BASED DISC ASSESSMENT MODEL

200

TRAINING AN ML-BASED MRS ACQUISITION DATA QUALITY EVALUATION MODEL

300

MODEL(S)

320 MODEL TRAINER

312 TRAINING DATA

310 TRAINING DATA GENERATOR

204 PROCESSED SPECTRUM DATA

302 GROUND TRUTH ACQUISITION QUALITY DATA

110 SIGNAL PROCESSOR

202 MRS ACQUISITION DATA

700

BEGIN ML-BASED DISC
ASSESSMENT ROUTINE — 702

OBTAIN SPECTRUM DATA — 704

706

EVALUATE QUALITY OF
SPECTRUM DATA USING MODEL

712

ASSESS DISC USING
SPECTRUM DATA AND MODEL

708

QUALITY
CRITERION
SATISFIED
?

YES

NO

710

REJECT SPECTRUM DATA INPUT

714

GENERATE DISC
ASSESSMENT OUTPUT

END — 716

SYSTEM FOR MACHINE LEARNING-BASED MODEL TRAINING AND PREDICTION FOR EVALUATION OF PAIN

CROSS-REFERENCE TO RELATED APPLICATION

The present application claims priority to U.S. Provisional Patent Application No. 63/263,321, filed Oct. 29, 2021, the contents of which are hereby incorporated by reference herein and made part of this specification.

BACKGROUND

Field of the Disclosure

This disclosure relates to systems and methods for measuring and evaluating chemical constituents in tissue. It also relates to novel applications of machine learning for developing new diagnostic approaches for evaluating the health or medical condition associated with a tissue, and including in particular as applied to magnetic resonance spectroscopy for evaluating intervertebral discs or other regions of interest.

Description of the Related Art

Magnetic resonance imaging (MRI) is a standard of diagnostic care for back pain. MRI in the context of back pain is sensitive to changes in disc and endplate hydration and structural morphology, and often yields clinically relevant diagnoses for certain specific pathophysiological spinal conditions such as spondylolisthesis and disc herniations with nerve root impingement (e.g., sciatica). In the particular context of primarily axial "discogenic" low back pain (DLBP), MRI is principally useful for indicating degree of disc degeneration. However, degree of disc degeneration has not been well correlated to pain. In one regard, people free of back pain often have disc degeneration profiles similar to those of people with chronic, severe axial back pain. Accordingly, a second line diagnostic exam called "provocative discography" (PD) is often performed after MRI exams in order to localize painful discs. This approach uses a needle injection of pressurized dye in awake patients in order to intentionally provoke pain. The patient's subjective reporting of pain level experienced during the injection (e.g., on increasing scale of 0-10) and concordance to usual sensation of pain is the primary diagnostic data used to determine diagnosis as a "positive discogram" indicating painful disc versus a "negative discogram" for a disc indicating it is not a source of the patient's chronic, severe back pain. Yet, while PD technique has been shown to be highly accurate, it still remains highly invasive, painful, risky, is often performed under X-ray visualization with high radiation exposure, and has been associated with accelerated degeneration of discs after receiving a diagnostic PD intervention. Accordingly, PD is controversial and often avoided, resulting in many patients either having unsuccessful surgery due to poor diagnostic direction or left untreated and in prolonged, debilitating pain.

SUMMARY OF SOME EMBODIMENTS

In some aspects, the techniques described herein relate to a diagnostic system for providing diagnostic information for a medical condition associated with a region of interest (ROI) in a patient, the diagnostic system including: a magnetic resonance spectroscopy (MRS) system configured to generate MRS acquisition data for a voxel located within the ROI; an MRS signal processor configured to process the MRS acquisition data to produce processed MRS spectrum data; and a diagnostic processor configured to: extract a subset of the processed MRS spectrum data corresponding to a chemical shift range of interest ranging from a lower chemical shift range boundary to an upper chemical shift range boundary, wherein the subset of the processed MRS spectrum data includes a plurality of data points, and wherein a data point of the plurality of data points represents an amplitude value associated with a chemical shift value within the chemical shift range of interest; generate a feature vector including representative values for each of a plurality of subranges of the chemical shift range of interest; process the feature vector using an ML model trained to determine, from the representative values for each of the plurality of subranges, a classification regarding the medical condition associated with the ROI; and generate the diagnostic information for the medical condition using the classification.

In some aspects, the techniques described herein relate to a computer-implemented method for providing diagnostic information for a medical condition associated with a region of interest (ROI) in a patient, the computer-implemented method including: obtaining, by a diagnostic system including computer-readable memory and one or more computer processors, processed MRS spectrum data representing output of a magnetic resonance spectroscopy (MRS) system, wherein the output of the MRS system includes MRS acquisition data for a voxel located within the ROI; extracting, by the diagnostic system, a subset of the processed MRS spectrum data corresponding to a chemical shift range of interest ranging from a lower chemical shift range boundary to an upper chemical shift range boundary, wherein the subset of the processed MRS spectrum data includes a plurality of data points, and wherein a data point of the plurality of data points represents an amplitude value associated with a chemical shift value within the chemical shift range of interest; generating, by the diagnostic system, a feature vector including representative values for each of a plurality of subranges of the chemical shift range of interest; processing, by the diagnostic system, the feature vector using an ML model trained to determine, from the representative values for each of the plurality of subranges, a classification regarding the medical condition associated with the ROI; and generating, by the diagnostic system, the diagnostic information for the medical condition using the classification.

In some aspects of this disclosure, a computer-implemented method is provided which comprises: under control of a computing system, including one or more computing devices configured to execute specific instructions, obtaining a corpus of training data pairs, wherein a training data pair of the corpus includes a training data input and a corresponding reference output, wherein the training data input is derived from a first diagnostic data set regarding a first physical parameter of a subject, and wherein the corresponding reference output includes a classification of the first physical parameter to which the training data input is to be mapped; and training a machine learning model using the corpus of training data pairs, wherein the machine learning model is trained to generate model output data representing a diagnostic assessment for a medical condition associated with the first physical parameter.

According to one mode of this aspect, the first physical parameter comprises a measurement or indicia associated with a tissue of a subject.

According to one embodiment of this mode, the measurement or indicia is associated with at least one of a structural integrity biomarker, a pain biomarker, and a degenerative pain biomarker for the tissue.

According to another embodiment, the tissue comprises an intervertebral disc.

According to another embodiment, the measurement or indicia is derived from a magnetic resonance spectroscopy (MRS) spectrum acquired from the tissue.

According to another embodiment, the medical condition comprises at least one of pain, degeneration, and degenerative pain.

According to another mode, the diagnostic assessment comprises a positive or negative classification for the presence or absence, respectively, of the medical condition.

Another aspect of this disclosure provides a system and method for diagnosing a medical condition in a patient, comprising: evaluating a first set of diagnostic data associated with at least one tissue structure in each of a first group of subjects; wherein at least a portion of the first set of diagnostic data is associated with the medical condition; evaluating a second set of diagnostic reference data that is also associated with the medical condition in the first group of subjects; comparing the first set and the second set; and determining a third set of criteria for at least a first portion of the diagnostic data that is correlative to at least a first portion of the reference data.

According to one mode of this aspect, the first set of diagnostic data comprises magnetic resonance spectroscopy (MRS) data.

According to another mode, the second set of diagnostic reference data comprises a set of treatment outcomes from treating the medical condition in each of the first group of subjects.

According to one embodiment of this mode: the at least one tissue structure comprises a plurality of separate tissue structures in each of the first group of subjects; the first set of diagnostic data comprises a set of diagnostic measurements for each of the tissue structures; the treatment outcomes are associated with localized treatments at a first sub-set of the tissue structures and with a second sub-set of the tissue structures left untreated; the comparing comprises correlating at least one of (a) a first range of treatment outcomes with at least a first feature of the first portion of the diagnostic data in the first sub-set of treated tissue structures, and (b) a second range of treatment outcomes with at least a second feature of the first portion of the diagnostic data in the second sub-set of untreated tissue structures.

Certain further features of this embodiment also comprise at least one of the following: the tissue structures comprise intervertebral discs, the first set of diagnostic data comprises magnetic resonance spectroscopy (MRS) data acquired from each of the discs, the treatment outcomes comprise at least one of visual analog scale (VAS) for back pain, Oswestry disability index (ODI) for back pain, a numerical or percentage change in either or both of VAS and ODI from pre-treatment baseline to post-treatment follow-up, a success or failure classification for each respective treatment outcome based on at least one threshold criterion for significant improvement based on at least one of VAS and ODI, or a combination of such VAS and ODI bases.

According to still further features, the treatment outcomes may comprise a success classification, and converse failure classification, based on post-treatment improvement of at least one of: a 15 point ODI reduction, a 20 point ODI reduction, a 1.5 point VAS, a 2.0 point VAS reduction, a 2.5 point VAS reduction, a post-treatment ODI below 40 points, or a post-treatment VAS below 4.0 points.

In some aspects, the techniques described herein relate to a computer-implemented method including: under control of a computing system including one or more computing devices configured to execute specific instructions, obtaining a corpus of training data pairs, wherein a training data pair of the corpus includes a training data input and a corresponding reference output, wherein the training data input is derived from first magnetic resonance spectroscopy (MRS) data regarding a first intervertebral disc, and wherein the corresponding reference output includes a classification of the first intervertebral disc to which the training data input is to be mapped; and training a machine learning model using the corpus of training data pairs, wherein the machine learning model is trained to generate model output data representing one of positive for pain or negative for pain.

BRIEF DESCRIPTION OF THE DRAWINGS

Embodiments of various inventive features will now be described with reference to the following drawings. Throughout the drawings, reference numbers may be reused to indicate correspondence between referenced elements. The drawings are provided to illustrate example embodiments described herein and are not intended to limit the scope of the disclosure.

DETAILED DESCRIPTION

The present disclosure is directed to use of machine learning (ML) to evaluate data generated by magnetic resonance imaging (MRI) systems, such as magnetic resonance spectroscopy (MRS) data. More specifically, ML-based systems and methods use MRS data (and optionally other data) to evaluate a medical condition associated with a region of interest (ROI) of a patient, such as intervertebral disc pain. An ML-based diagnostic system can evaluate MRS spectra using one or more algorithms, in some cases using ML models trained to classify the MRS spectra based on diagnostic and/or outcome-based ground truth data. Advantageously, this provides detection of patterns in data that may not be detected by manual analysis, and allows for continual feedback and improvement of the classification models and algorithms. Additionally, or alternatively, an ML-based diagnostic system can evaluate acquired MRS data to assess the quality of the procedure by which the MRS data was generated or whether the MRS data generated therefrom is to be used in disc assessment. For example, the system may detect "technical failures," such as excessive endplate lipids (e.g., from poor voxel positioning), low signal-to-noise ratio, poor shim (from the MRI scanner), and/or spectral artifacts. Beneficially, detection of such conditions may trigger a re-scan or other remedial action that can be performed while the patient is still available, rather than being manually detected afterwards and resulting in a lost opportunity to assess pain.

Various aspects of the disclosure will now be described with regard to certain examples and embodiments, which are intended to illustrate but not limit the disclosure. Although aspects of some embodiments described in the disclosure will focus, for the purpose of illustration, on particular examples of MRS data, ground truth data, algorithms, ML models, and training and classification routines, the examples are illustrative only and are not intended to be limiting to the broader aspects of this disclosure (albeit while certain such specific, detailed embodiments may be considered uniquely novel and beneficial). In some embodiments, the techniques described herein may be applied to additional or alternative MRS data, ground truth data, algorithms, ML models, training and classification routines, and the like. In addition, any feature, process, device, or component of any embodiment described and/or illustrated in this specification can be used by itself, or with or instead of any other feature, process, device, or component of any other embodiment described and/or illustrated in this specification.

Example Execution Environment

Figure 1A:
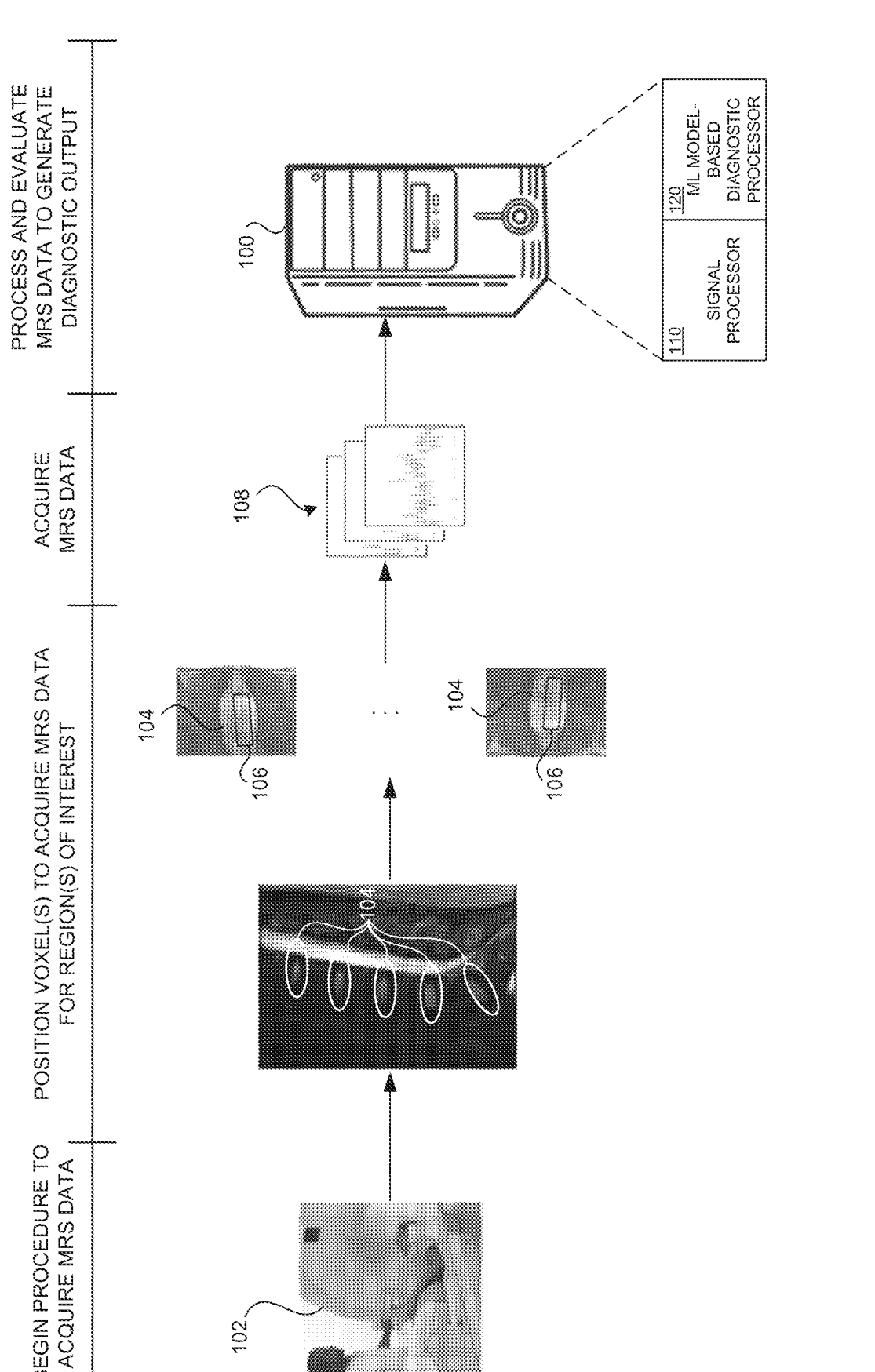
FIG. 1A is a diagram illustrating aspects of a magnetic resonance spectroscopy procedure, and machine learning model-based analysis of data acquired through the procedure according to some embodiments.

FIG. 1A shows a general overview of a procedure for generating MRS data regarding one or more ROIs, and evaluating the MRS data using an ML-based diagnostic system 100.

In some embodiments, as shown, an MRS system 102 may be used to begin an MRS procedure on a patient. Instead of (or in addition to) image-based output, the MRS system 102 may be configured to produce MRS data regarding a ROI of the patient. To obtain MRS data for an ROI, a voxel 106 may be defined and MRS data 108 may be acquired, as described herein. For example, a voxel 106 may be defined to acquire MRS data 108 for an intervertebral disc 104. If multiple intervertebral discs 104 are to be evaluated, then multiple voxels 106 may be defined and multiple sets of corresponding MRS data 108 may be acquired (e.g., at least one voxel 106 for each intervertebral disc 104).

Although the illustrated example shows the ROIs as a set of intervertebral discs 104 of a patient, the example is provided for illustrative purposes only and is not intended to be limiting, required, or exhaustive. In some embodiments, the ML-based diagnostic system 100 may be used to evaluate MRS data regarding other ROIs.

The acquired MRS data (also referred to herein as "MRS acquisition data" or simply as "acquisition data" for brevity) may be processed by the ML-based diagnostic system 100 (also referred to herein simply as a "diagnostic system" for brevity). The diagnostic system 100 may include various subsystems for processing acquisition data and generating diagnostic output. For example, the diagnostic system 100 may include a signal processor 110 to process the acquisition data and generate processed MRS data (also referred to as "spectrum data"). The diagnostic system 100 may also include an ML model-based diagnostic processor 120 (also referred to herein simply as a "diagnostic processor" for brevity) that evaluates the spectrum data using one or more ML models. In some embodiments, the ML models may generate model output data representing diagnostic classifications (e.g., positive or negative for pain in a ROI), acquisition quality classifications (e.g., positive or negative for indicators of low-quality acquisition data), or both. The diagnostic system 100 may use the model output data to generate diagnostic output.

Figure 8:
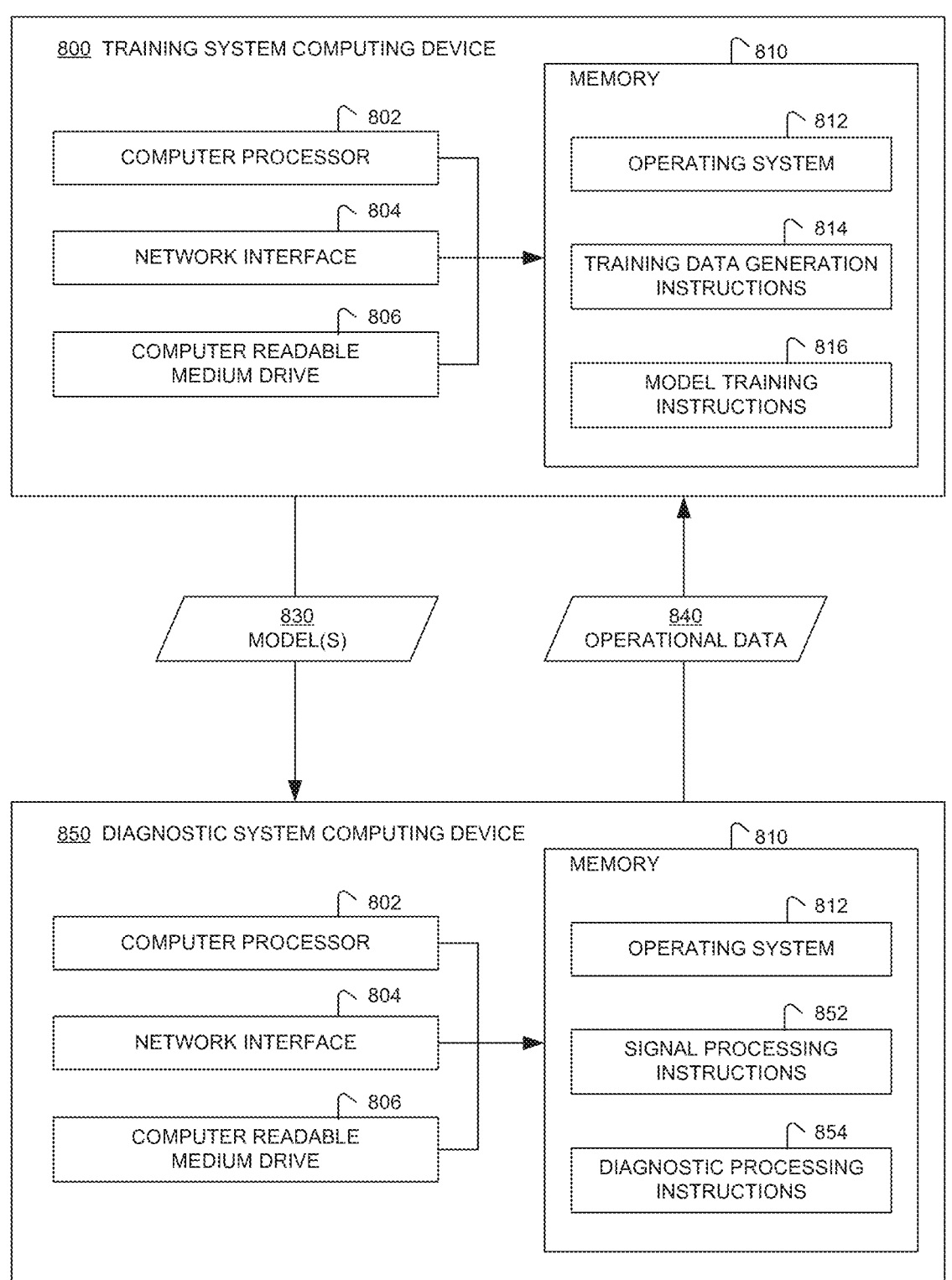
FIG. 8 illustrates various components of example computing systems configured to implement aspects of the present disclosure according to some embodiments.

The diagnostic system 100 may be a logical association of one or more computing systems for processing acquisition data and generating diagnostic output using ML models. The diagnostic system 100 (or individual components or subsystems thereof) may be implemented on one or more physical computing systems such as blade servers, midrange computing devices, mainframe computers, desktop computers, or any other computing device configured to provide computing services and resources. One example of a diagnostic system computing device 850 on which the diagnostic system 100 may be implemented is shown in FIG. 8. The diagnostic system 100 may include any number of such computing devices.

In some embodiments, the features and services provided by the diagnostic system 100 may be implemented as web services consumable via one or more communication networks. In further embodiments, the diagnostic system 100 (or individual components thereof) are provided by one or more virtual machines implemented in a hosted computing environment. The hosted computing environment may include one or more rapidly provisioned and released computing resources, such as computing devices, networking devices, and/or storage devices. A hosted computing environment may also be referred to as a "cloud" computing environment.

Figure 1B:
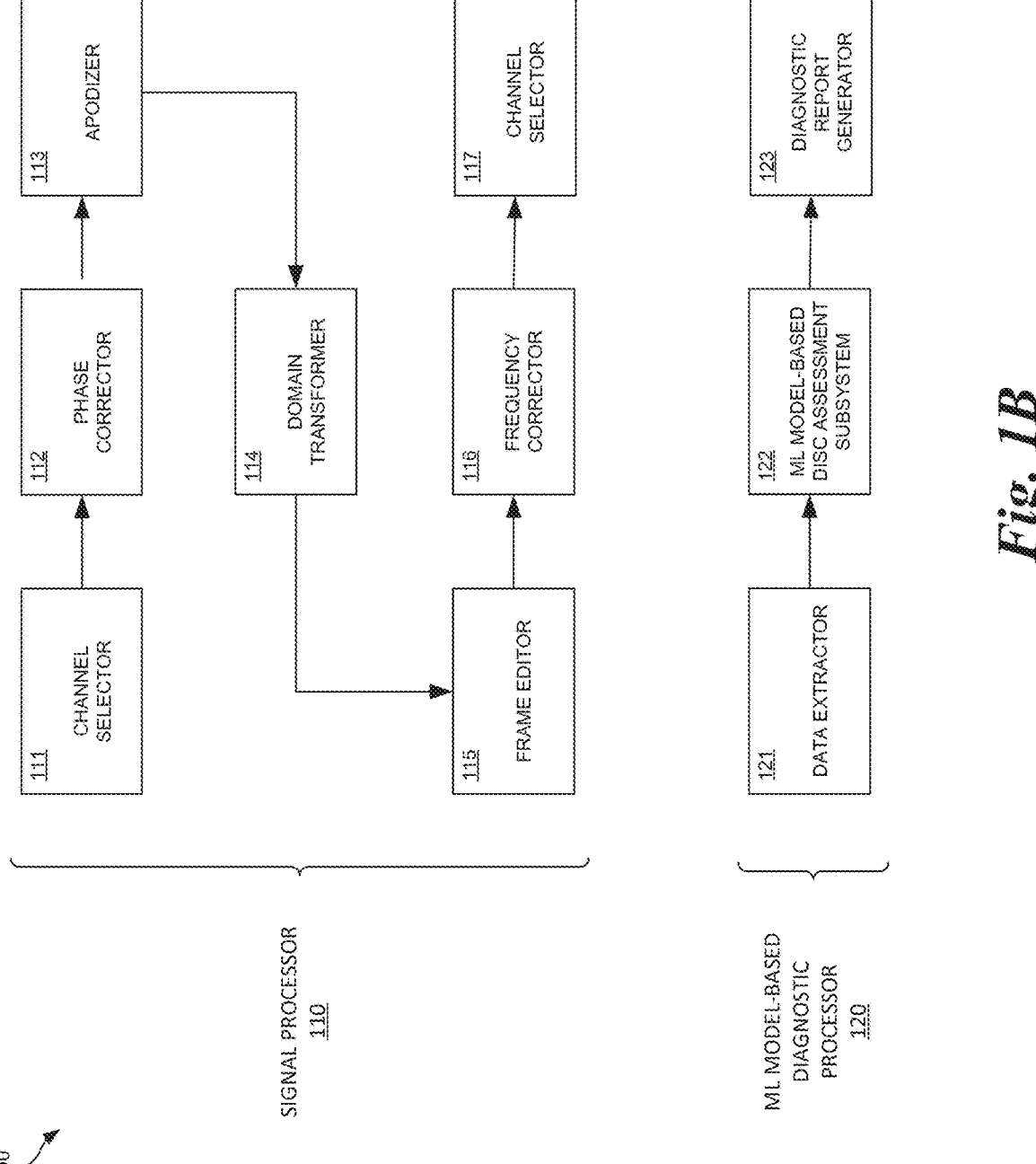
FIG. 1B is a block diagram illustrating various components of a signal processor and a machine learning model-based diagnostic processor according to some embodiments.

FIG. 1B shows a general schematic overview for the processing flow of the diagnostic system 100 to process acquisition data and generate diagnostic output. The signal processor 110 may include various sub-components and processors that carry out certain steps, such as a channel selector 111 that conducts channel or "coil" selection, phase corrector 112 that does phase correction, apodizer 113 that conducts apodization, domain transformer 114 that conducts domain transformation (e.g., transformation of data from time domain to frequency domain), frame editor 115 that conducts frame editing, frequency corrector 116 that conducts frequency correction, and channel combiner 117 that conducts combining or averaging steps to aggregate retained channels into one final post-processed spectral results (not shown). The post-processed spectral results may be referred to as spectrum data.

Following the signal processing steps, the diagnostic processor 120 may conduct diagnostic processing of the spectrum data using a data extractor 121, an ML model-based disc assessment subsystem 122, and a diagnostic report generator 123. The data extractor 121 may process spectrum data into a form that that may be input into the ML model-based disc assessment subsystem 122, which may evaluate the input data and assess one or more ROIs. The diagnostic report generator 123 may produce an output presentation based on output of the ML model-based disc assessment subsystem 122.

The components illustrated in FIG. 1B are illustrative only, and are not intended to be limiting, required, or exhaustive. In some embodiments, additional, fewer, and/or alternative components may be used. Some embodiments of the components illustrated in FIG. 1B, and examples of the operations performed by the components, are described in U.S. Patent Application Publication No. 2019/0307393, which is incorporated by reference herein and forms part of this specification. U.S. Pat. Nos. 10,285,622; 9,280,718; 10,045,711; and 9,901,285 are hereby incorporated by reference herein and form part of this specification. The systems and methods disclosed herein can use various features disclosed in these references.

In some embodiments, as described in U.S. Patent Application Publication No. 2019/0307393, for example, the signal processor 110 is configured to generate a diagnostically useful MRS spectrum from a voxel located principally within an intervertebral disc of a patient. The MRS spectrum data may be used for measuring spectral information corresponding to various chemicals (e.g., propionic acid (PA), lactic acid (LA), alanine (AL), and structural chemicals of proteoglycan (PG) and collagen or carbohydrate (CA)) to diagnose and/or monitor various conditions. Certain applications include diagnosing painful and non-painful discs in chronic, severe low back pain patients (DDD-MRS). The signal processor 110 generates or otherwise acquires DDD-MRS spectra within intervertebral disc nuclei to produce a processed spectrum, with spectral regions corresponding to certain chemicals. An ML model-based diagnostic processor 120 may then determine a diagnostic classification for each disc using one or more ML models as described in greater detail below. Diagnostic information may then be presented and used in a manner that is helpful for distinguishing degenerative painful vs. non-painful discs. For example, a diagnostic display may provide a scaled, color coded legend and indication of results for each disc analyzed, which is shown with and/or as an overlay onto an MRI image of the lumbar spine region for the patient being evaluated. Clinical application of the embodiments provides a non-invasive, objective, pain-free, reliable approach for diagnosing painful vs. non-painful discs by simply extending and enhancing the utility of otherwise standard MRI exams of the lumbar spine, and/or monitoring such chemicals.

ML Model Training for Disc Assessment

Figure 2:
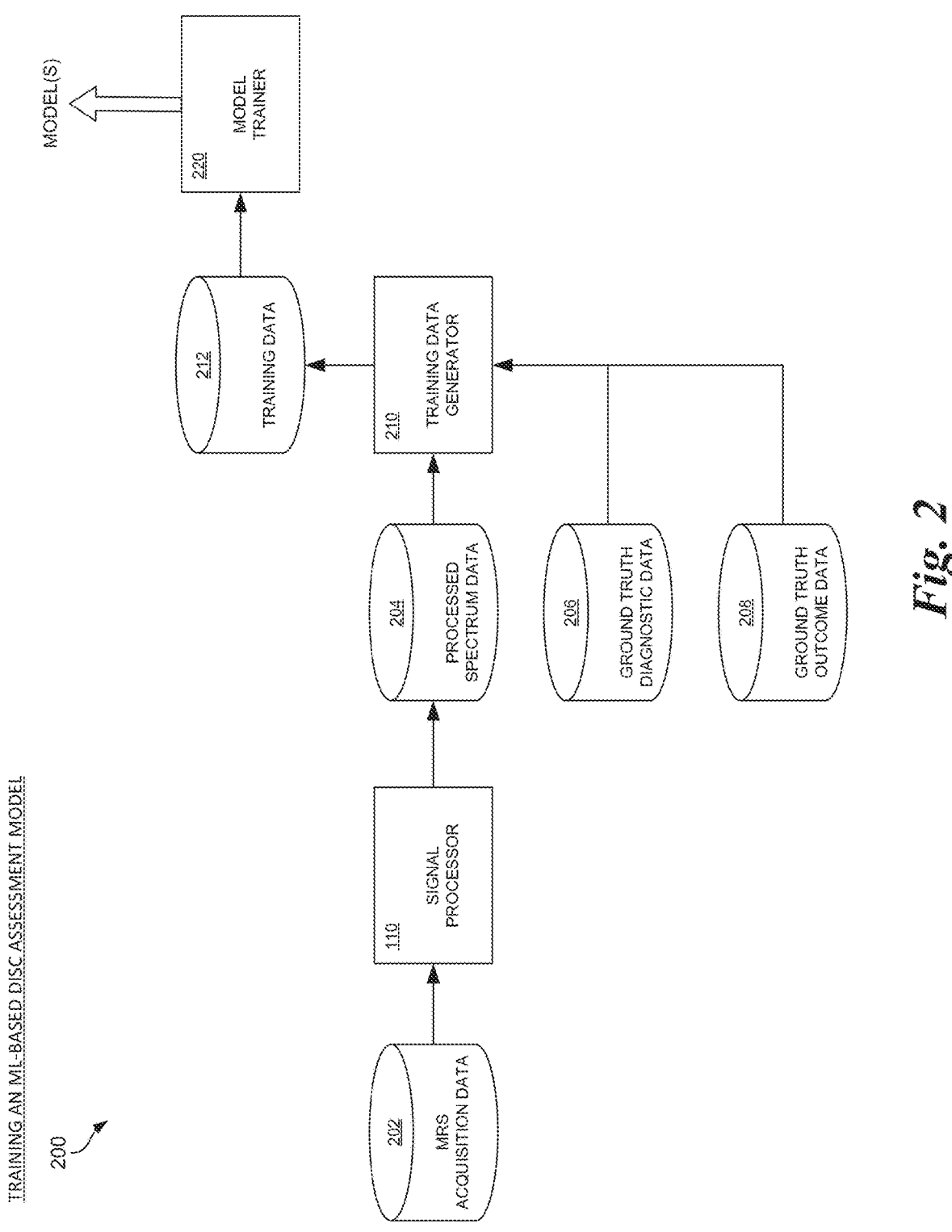
FIG. 2 is a block diagram illustrating data flows and interactions of various computing components to train a machine learning based system for assessing a medical condition associated with a region of interest according to some embodiments.

With reference to an illustrative embodiment, FIG. 2 shows example data flows and interactions for training a machine learning model to evaluate spectrum data and assess ROIs, such as intervertebral discs. Advantageously, one or more ML models may be trained to classify spectrum data as indicative of particular medical conditions (e.g., painful discs) based on correlations of the spectrum data to ground truth diagnostics (e.g., provocative discography results) and/or treatment outcomes (e.g., outcomes from surgery, physical therapy, regenerative cell therapies).

Training data may be obtained by performing MRS procedures on patient discs, and also obtaining corresponding diagnostic data and/or treatment outcome data for the discs. Illustratively, the training data may include, for individual discs, a pair of training data items including a training data input item (e.g., a feature vector) and a corresponding reference data output item (e.g., a reference data vector or other representation of a correct or desired classification result) mapped to the training data input item.

Generally described, training an ML model (also referred to herein simply as a "model" for brevity) may involve a variety of different operations, depending upon the particular type of model being trained. For example, if the model is a naïve Bayesian classifier, then training may include analyzing features of the training data to determine various statistical properties of the training data. These statistical properties can be used as parameters of a probabilistic Bayesian classifier, such as a multinomial naïve Bayesian classifier or a Gaussian naïve Bayesian classifier. As another example, if the model is a support vector machine (SVM) or a neural network, then training may include an iterative process in which training data input items are analyzed using a current set of model parameters (which may, in the initial iteration, be set to default or random values) and analyzed against corresponding reference data output items using an objective function (also referred to as a "loss" function). Based on objective function analysis, parameters of the model may be adjusted such that in the next iteration the training output will be closer to the reference output. The iterations may continue until a stopping criterion is reached (e.g., the accuracy performance across a number of test inputs satisfies a threshold). The example training methods described herein are illustrative only, and are not intended to be limiting, required, or exhaustive of the training methods and models that may be used.

FIG. 2 illustrates a set of input MRS acquisition data 202 (also referred to as "raw" MRS data) generated from performing MRS procedures on patients. In some embodiments, an operator may orient a voxel 106 on display of a patient's spinal anatomy to obtain MRS acquisition data 202 for the region within the voxel 106. The MRS acquisition data 202 generated by the MRS procedure may represent measurements of various chemicals in the tissue within the voxel, such as PG, LA, AL, PA, multi-chemical ranges (e.g., LAAL, a range capturing both LA+AL peaks; or ALPA, a range capturing each of AL+LA+PA peaks) etc.

The MRS acquisition data 202 may be processed by the signal processor 110 to produce processed MRS spectrum data 204 (also referred to herein as "processed spectrum data" or simply as "spectrum data"). For example, the signal processor 110 may produce processed spectrum data 204 by performing signal conditioning, frequency correction, phase correction, frame editing, and the like, as described in greater detail in U.S. Patent Application Publication No. 2019/0307393.

The processed spectrum data 204 may be generated in the form of a set of data points that correspond to a plot of a spectrum. In some embodiments, the processed spectrum data 204 may be a set of points defined by multidimensional coordinates, such as (x, y) pairs where the x value of a given data point represents a chemical shift represented by the data point, and the y value represents an amplitude. For example, the processed spectrum data 204 may include any consistent quantity of points, including but not necessarily limited to powers of 2, such as 8, 10, 12, 20, 25, 50, 64, 100, 128, 200, 256, 500, 512, 1000, 1024, 2048, etc. However, the points may not necessarily include x values that are consistent across sets of processed spectrum data 204 (e.g., for different discs, or even for different sets of processed spectrum data 204 for the same disc). Thus, in order to ensure that evaluation of the processed spectrum data 204 is consistent, the data extractor 121 may further process the processed spectrum data 204 to standardize the data as described in greater detail herein and produce a feature vector for analysis by one or more ML models.

FIG. 2 further illustrates various categories of ground truth data for use in training one or more models. Ground truth diagnostic data 206 may include data regarding results of one or more diagnostic tests performed on the discs represented by the MRS acquisition data 202 and corresponding processed spectrum data 204. For example, provocative discography (PD) may be performed on each disc, and the results as either positive or negative for pain may be recorded as ground truth diagnostic data 206.

Ground truth outcome data 208 may include data regarding outcomes of one or more treatments, or outcomes in the absence of any treatment. Such data may be obtained as feedback after the diagnostic system 100 has generated model output for discs. For example, an ML model may be trained to classify spectrum data as indicative of painful discs based on correlations of the spectrum data to ground truth diagnostics (e.g., provocative discography results), as described herein. Subsequently, treatments may or may not be applied, and follow-up diagnostics may be performed to assess whether (or the relative extent by which) pain experienced pre-treatment has been reduced or eliminated post-treatment. Ground truth outcome data 208 may be generated based on such outcomes, and the ML model may be retrained using the ground truth outcome data 208 instead of—or in addition to—the ground truth diagnostic data 206 originally used to train the model. The feedback loop and retraining process may continue as desired.

With reference to an illustrative example, one or more treatments such as surgery, physical therapy, and/or regenerative cell therapy (or other forms of injectable biologics or other therapeutic injectables) may be performed on a disc, and results of the treatment(s) as negative for pain or continued positive for pain (or by reference to degree of change) may be recorded as ground truth outcome data 208. If a reduction or elimination of pain was achieved after treatment of the disc, then this outcome may be considered confirmation that the disc was painful and ground truth classification for the corresponding training data input for the disc may be set as a positive classification for pain. If no pain reduction was achieved after the treatment, this can be considered indicative of the disc not being a painful disc, and the ground truth classification may be set as a negative classification for pain. However, it will be appreciated that surgery and other treatments have their own risks and rates of effectiveness, and a failure to reduce pain does not necessarily indicate the treated disc itself was not the cause (or a contributing cause) of pain. Thus, in some embodiments the outcome of a treatment may be considered as one factor in an overall determination of a ground truth classification for the disc. Alternatively, a relatively large training set may be able to overcome such limitations and produce accurate output even with sporadic observation of ineffective treatment on actually painful discs.

While certain such examples are also described by reference to more binary forms of outcomes classifications, e.g., success or failure, presence or absence of pain, it is also contemplated that pain is not binary, but a relative metric on a sliding scale (e.g., visual analog scale for pain having a 0-10 point range). Accordingly, ground truths used for training may not necessarily be based on such binary classifications, but based on relative changes and those respective correlations to diagnostic data.

As another example, no surgery or other treatment may be applied to a disc identified as painful. If after passage of a predetermined or dynamically-determined period of time (e.g., days, weeks, months, etc.) there is still pain reported, then the ground truth classification for the corresponding training data input for the disc may be set as a positive classification for pain. If treatment was applied to a different disc and resulted in a reduction or elimination of pain, then the ground truth classification for the corresponding training data input for the untreated disc may be set as a negative classification for pain.

To determine whether or not a treatment (or omission thereof) resulted in a reduction in pain such that ground truth outcome data 208 can be generated or modified, various metrics may be obtained or otherwise considered. In some embodiments, a Visual Analog Scale (VAS) may be used to assess pain pre- and post-treatment. For example, a patient may report pain on a 10-point VAS. If reported post-treatment pain shows an improvement of at least a threshold point value or percentage (e.g., 1.5-2.5 points, typically at least 2 points), then the outcome may be considered positive and the ground truth outcome data 208 for the treated disc may be set to a positive classification for significant pain relief, or the ground truth outcome data 208 for the feature vector of the disc prior to treatment may be set to (or confirmed as) a positive classification for pain; otherwise, the ground truth outcome data 208 for the treated disc may be set to a negative classification indicative of failed or insignificant pain relief, or the ground truth outcome data 208 for the feature vector of the disc prior to treatment may be set to (or confirmed as) a negative classification for pain. As another example, if reported post-treatment pain satisfies a threshold (e.g., less than or equal to 4 on the VAS scale), then the outcome may be considered positive and the ground truth outcome data 208 for the treated disc may be set to a positive classification for significant pain relief, or the ground truth outcome data 208 for the feature vector of the disc prior to treatment may be set to (or confirmed as) a positive classification for pain; otherwise, the ground truth outcome data 208 for the treated disc may be set to a negative classification indicative of failed or insignificant pain relief, or the ground truth outcome data 208 for the feature vector of the disc prior to treatment may be set to (or confirmed as) a negative classification for pain.

In some embodiments, the Oswestry Disability Index (ODI), typically measured on 0-100 point scale, may be used to assess the extent of patient disability as affected by pain pre- and post-treatment. For example, a patient may report ODI scores at both pre-treatment baseline and post-treatment follow-up. If reported post-treatment pain shows an improvement of at least a threshold point value or percentage (e.g., 15-25 points, typically at least 20 points), then the outcome may be considered positive and the ground truth outcome data 208 for the treated disc may be set to a positive classification for significant pain relief, or the ground truth outcome data 208 for the feature vector of the disc prior to treatment may be set to (or confirmed as) a positive classification for pain; otherwise, the ground truth outcome data 208 for the treated disc may be set to a negative classification indicative of failed or insignificant pain relief, or the ground truth outcome data 208 for the feature vector of the disc prior to treatment may be set to (or confirmed as) a negative classification for pain. As another example, if reported post-treatment pain satisfies a threshold (e.g., less than or equal to 40 on the ODI), then the outcome may be considered positive and the ground truth outcome data 208 for the treated disc may be set to a positive classification for significant pain relief, or the ground truth outcome data 208 for the feature vector of the disc prior to treatment may be set to (or confirmed as) a positive classification for pain;

otherwise, the ground truth outcome data 208 for the treated disc may be set to a negative classification indicative of failed or insignificant pain relief, or the ground truth outcome data 208 for the feature vector of the disc prior to treatment may be set to (or confirmed as) a negative classification for pain. It is to be appreciated, however, that such classifications based on ODI relate to pain relief only indirectly to the extent reduction in pain translates to reduction in those measures for functionality and quality of life that are factored in the calculated ODI scores for disability.

In some embodiments, a combination of outcome-based analyses may be considered when determining ground truth outcome data 208. For example, both VAS and ODI metrics may be determined. If at least one of the two metrics satisfies a pain improvement criterion, then the outcome may be considered positive and the ground truth outcome data 208 for the treated disc may be set to a positive classification for significant pain relief, or the ground truth outcome data 208 for the feature vector of the disc prior to treatment may be set to (or confirmed as) a positive classification for pain; otherwise, the ground truth outcome data 208 for the treated disc may be set to a negative classification indicative of failed or insignificant pain relief, or the ground truth outcome data 208 for the feature vector of the disc prior to treatment may be set to (or confirmed as) a negative classification for pain. The examples of outcome-based analyses described herein are illustrative only, and are not intended to be limiting, required, or exhaustive. In some embodiments additional, fewer, and/or alternative outcome-based analyses may be used to generate ground truth outcome data 208.

A training data generator 210 may generate a corpus of training data for training one or more models. The specific format of training data may depend on the particular type of model being trained. Illustratively, the corpus of training data may include a pair of a training data input item and a corresponding reference data output item for each disc that is part of the training set.

Figure 5:
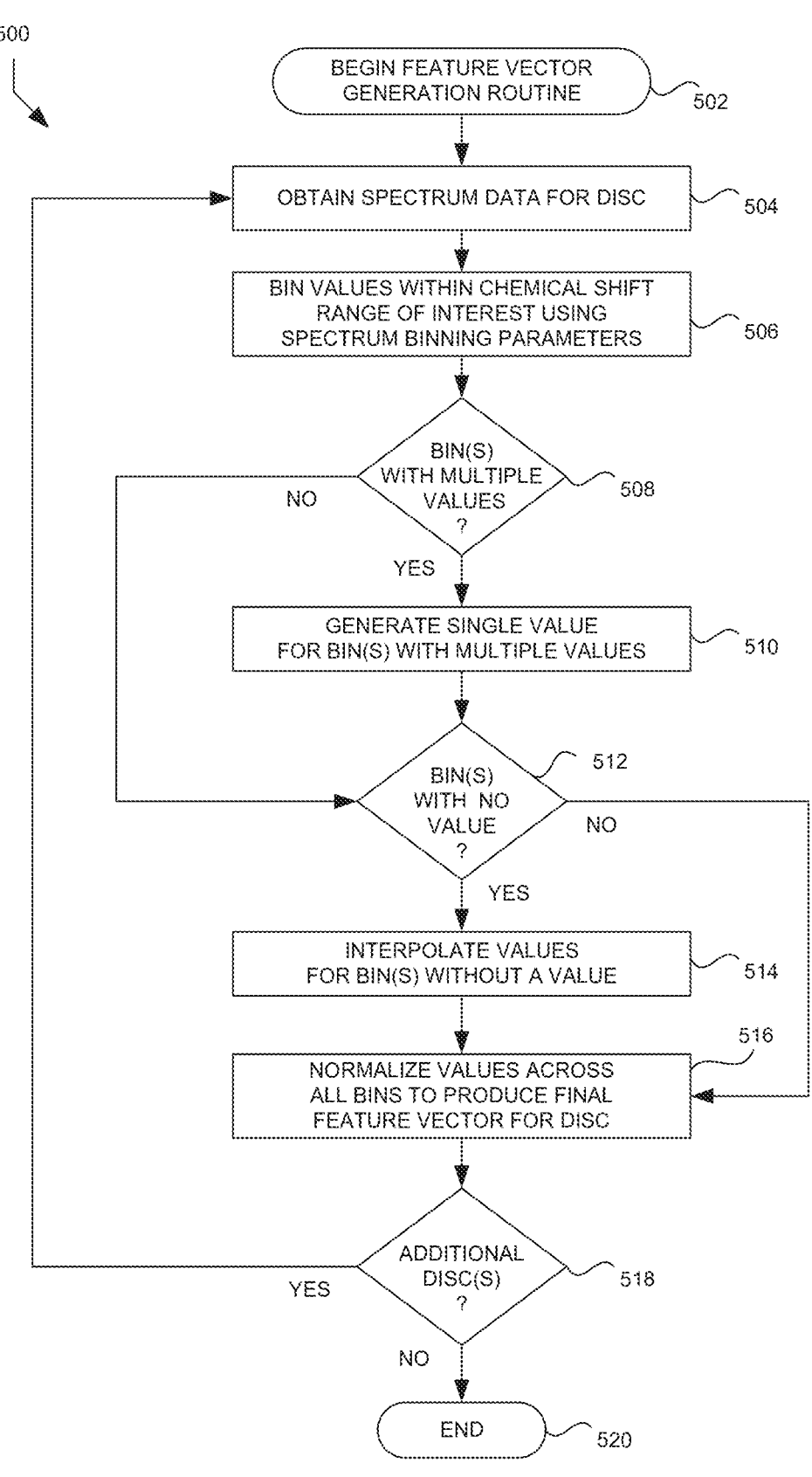
FIG. 5 is a flow diagram of an illustrative routine for generating a feature vector from magnetic resonance spectroscopy data to be evaluated using a machine learning model according to some embodiments.

In some embodiments, a training data input item may be a feature vector composed of multiple elements, where individual elements represent the values of individual bins of processed spectrum data 204. An example routine for generating a feature vector to represent processed spectrum data 204 for a particular disc is shown in FIG. 5.

In some embodiments, raw MRS acquisition data 202, or MRS acquisition data that has undergone different combinations of processing, may be used to generate training data instead of—or in addition to—processed MRS spectrum data 204. For example, raw MRS acquisition data 202 may undergo signal conditioning, frequency correction, and phase correction, and the result (with or without performing frame editing) may be used to generate training data input vectors composed of elements that correspond to values extracted from the data. The example combinations of processing that may be applied to MRS acquisition data 202 to generate training data as described herein are illustrative only, and are not intended to be limiting, required, or exhaustive. In some embodiments, other combinations of processing operations may be performed, such as any combination or sequence of operations described with respect to the signal processor 110 subsystems shown in FIG. 1B.

In some embodiments, a training data input item may include one or more data items in addition to those representing processed MRS spectrum data 204. For example, data regarding patient characteristics may be included, such as values representing one or more of: height, weight, body mass index (BMI), age, gender, race, comorbidities (e.g., other ailments, treatment, surgeries such as hip or knee replacement, spinal fusion, etc.), smoking status, alcohol/drug use status, diagnosis of systemic inflammation such as neuralgia, other patient characteristics, or some combination thereof. As another example, information regarding disc characteristics other than MRS spectrum data may be included, such as values representing one or more of: disc height, degree of hydration of the disc, other properties determined through MRI or MRS, identified anatomic level of the disc (e.g., L1-L2 disc), presence or absence of herniations, annular tears, or adjacent Modic end-plate changes, feature vectors or other representations of MRS spectrum data for other discs of same patient (e.g., to effectively normalize input across discs for a particular patient), other disc properties, or combinations thereof. The examples of patient and disc characteristics described herein are illustrative only, and are not intended to be limiting, required, or exhaustive. In some embodiments additional, fewer, and/or alternative patient or disc characteristics may be considered and represented in the feature vectors.

For each training data input item (e.g., for each feature vector generated from processed spectrum data), a corresponding reference data output item may include an indication of whether the disc is positive for pain as determined by a diagnostic test (e.g., PD) and/or an indication of whether pain remained after treatment of the disc. For example, the reference data output item may be a binary value, where 1 or True represents positive for pain, and 0 or False represents negative for pain.

In some embodiments, the training data generator 210 may reserve a portion of the training data pairs to be used to test the trained model(s). For example, the training data generator 210 may have access to MRS spectrum data and corresponding ground truth data for n discs. The training data generator 210 may reserve n/5 training data pairs to be used to test the model after training the model using all of the training data pairs, or after training the model using only the remaining 4n/5 training data pairs (e.g., five-fold cross validation). As another example, the training data generator 210 may reserve n/10 training data pairs to be used to test the model after training the model using all of the training data pairs, or after training the model using only the remaining 9n/10 training data pairs (e.g., ten-fold cross validation). In some embodiments, results of performing a cross validation process may include probability estimates for classification determinations made by the trained ML model. The probability estimates may be used as indicators of the degree of confidence in the classification determinations made at inference time by a diagnostic system 100 using the trained ML learning model.

Figure 4:
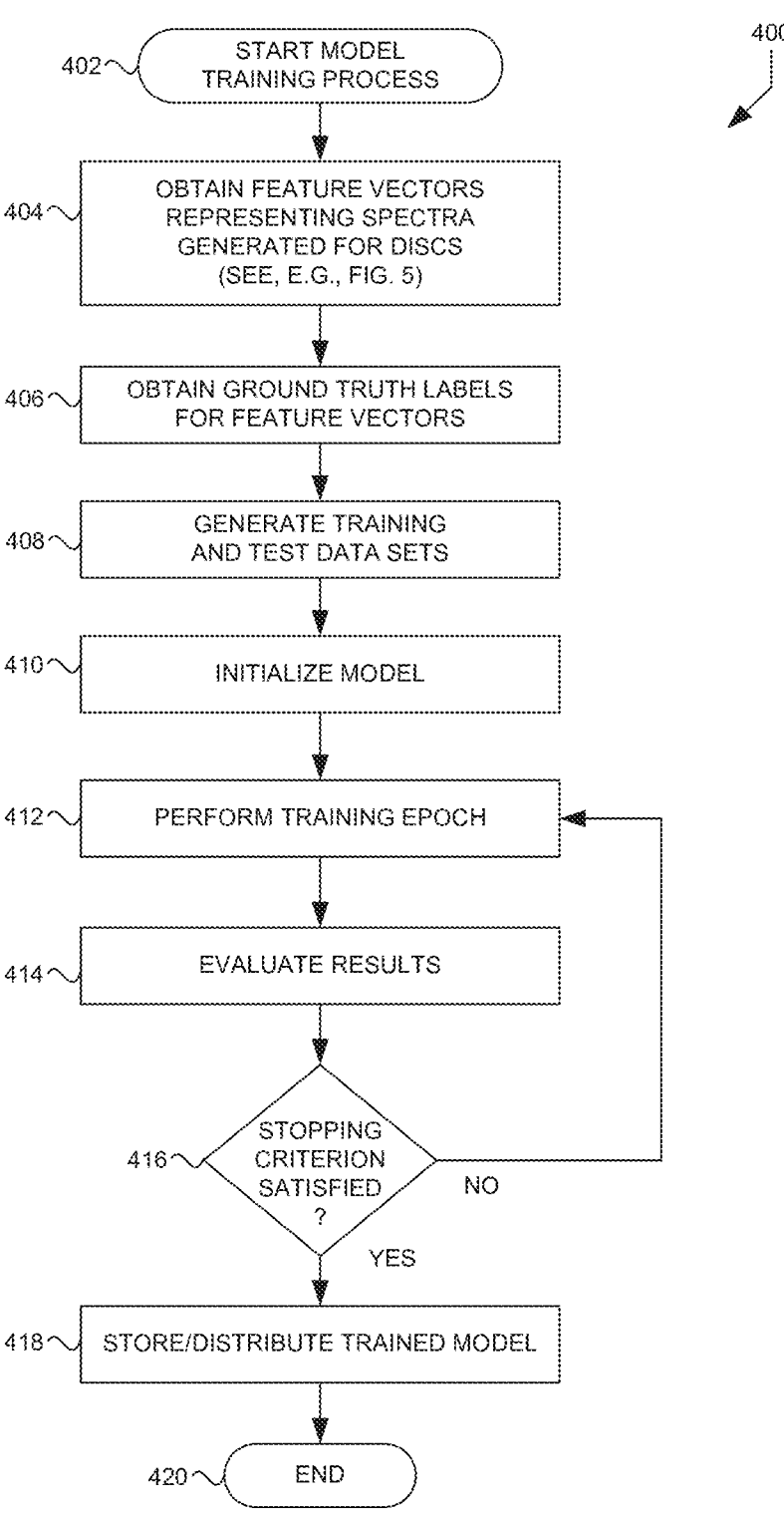
FIG. 4 is a flow diagram of an illustrative routine for training a machine learning model to evaluate magnetic resonance spectroscopy data according to some embodiments.

The model trainer 220 may use training data 212 generated by the training data generator 210 to train one or more models. An example training algorithm is illustrated in FIG. 4. The specific algorithm for training depends on the particular type of model being trained.

Figure 6:
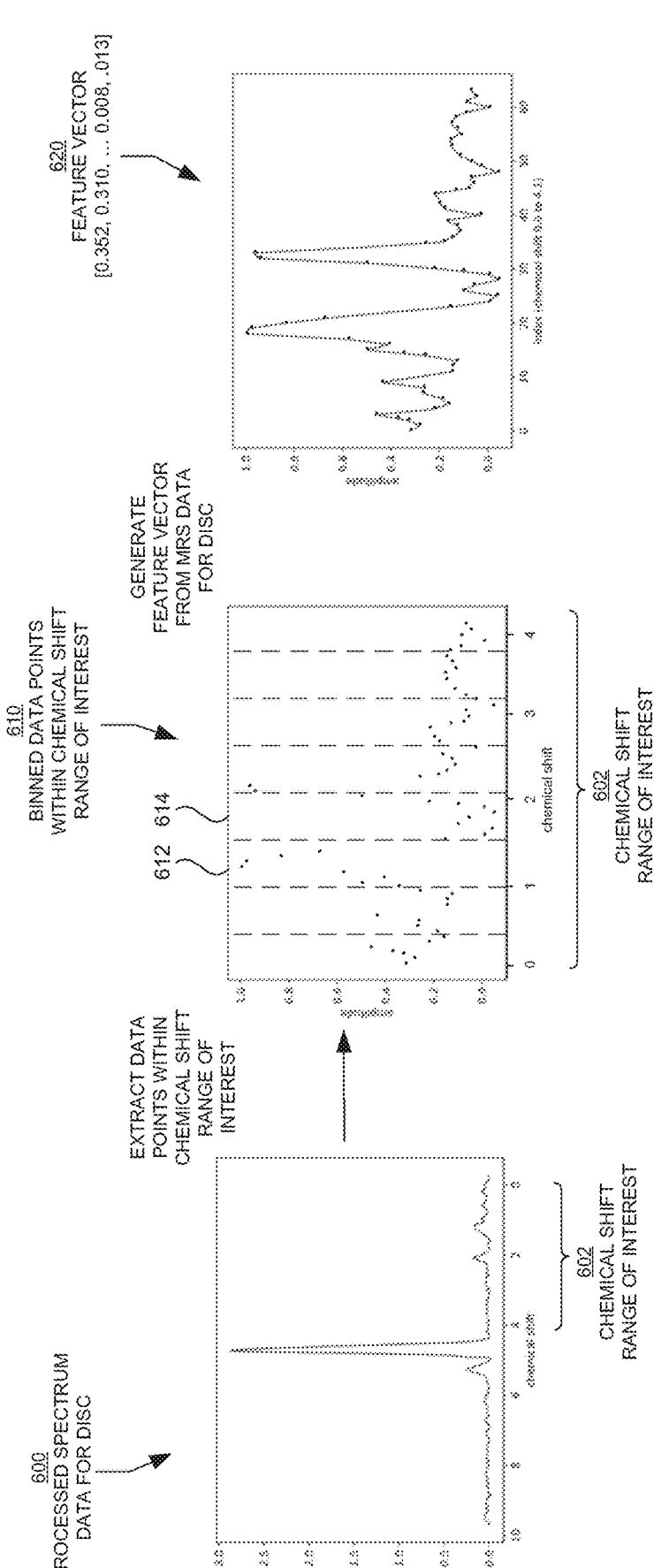
FIG. 6 illustrates generation of a feature vector from magnetic resonance spectroscopy data according to some embodiments.

In one embodiment, the model trainer 220 may train an SVM to classify binned MRS spectrum data, represented by feature vector, as either positive for pain or negative for pain. For example, the training data input items may be n-dimensional feature vectors with values for data extracted from MRS spectrum data (e.g., values representing amplitudes within a frequency band of interest, also referred to as a chemical shift range of interest, as shown in FIGS. 5 and 6). Thus, the training data input items may represent points in n-dimensional space. The reference data output items may be binary classification values. To distinguish between classes of discs (e.g., positive and negative for pain), an n-dimensional hyperplane is identified that provides the maximum margin (e.g., the maximum distance) between data points of the classes. The hyperplane may be determined using an objective function such as a hinge loss function.

In one embodiment, the model trainer 220 may train a neural network to classify binned MRS spectrum data, represented by feature vector, as either positive for pain or negative for pain. For example, the training data input items may be n-dimensional feature vectors with values for data extracted from MRS spectrum data (e.g., values representing amplitudes within a frequency band of interest, also referred to as a chemical shift range of interest, as shown in FIGS. 5 and 6). The reference data output items may be binary classification values. To distinguish between the classes of discs (e.g., positive and negative for pain), a multi-layer neural network is used in which each layer has a quantity of nodes, which may or may not be consistent across layers. Each node of the internal or "hidden" layer(s) corresponds to application of an activation function (e.g., rectified linear unit (ReLU)) and a bias term, and values from nodes in prior layers are passed to nodes in subsequent layers based on application of a weight. The output layer includes a single node that uses an activation function such as a sigmoid function to produce a value in the range [0, 1], where values less than a threshold (e.g., 0.5) are rounded down to 0 as the final classification output, and values equal to or greater than the threshold are rounded up to 1 as the final classification output. Feature vectors may be evaluated using a forward pass of the neural network to produce training data output (e.g., binary classification values). The classification output may be evaluated against the corresponding reference data output items using an objective function, such as cross-entropy loss. A gradient descent algorithm may be used to update the parameters of the neural network via backpropagation based on a gradient of the objective function.

The example models and training routines described herein are illustrative only, and are not intended to be limiting, required, or exhaustive. In some embodiments, other models may be used instead of the neural network and SVM-based models described above. For example, the model trainer 220 may train a Bayesian classifier, a linear regression model, or logistic regression model to classify binned MRS spectrum data as either positive for pain or negative for pain.

In some embodiments, an ensemble technique may be employed in which multiple algorithms or models are used. While individual ML models and training algorithms have their own limitations, using an ensemble of multiple such algorithms and/or models may provide better overall accuracy in classifying MRS spectrum data as indicative of whether a disc is painful or not painful. For example, a tree-based ensemble (e.g., random forest, extra-trees ensemble, regression trees, etc.) may be implemented in which subsets of features are used to build multiple split tress: one tree may use a first spectral band or subrange of a chemical shift range, another tree may use a second spectral band or subrange of a chemical shift range, another tree may use patient information, etc. As another example, one tree may use PG values, another tree may use LA values, another tree may use AL values, another tree may use a combination of LA and AL values (LAAL), another tree may apply different calculations or thresholds to PG, LA, AL, or other values, etc. Other types of ensemble models may be used, such as boosting ensembles (AdaBoost), max voting ensembles, and the like.

In some embodiments, a Receiver Operating Characteristic (ROC) curve may be used to evaluate the performance of a model in a validation procedure. Based at least partly on the ROC curve, the best performing model or ensemble model may be deployed for use.

Generally described, an ROC curve is based on the true positive rate (TPR) and false positive rate (FPR) of the classifier being evaluated. The TPR is the rate at which the classifier produces a "true positive" classification result (e.g., input data representing a truly painful disc is correctly classified as positive for pain) in relation to the total quantity of true positives and false negatives (e.g., input data representing a truly painful disc is incorrectly classified as negative for pain). The TPR may also be referred to as "sensitivity." The FPR is the rate at which the classifier produces a positive classification that is incorrect (e.g., input data representing a disc that is not painful is incorrectly classified as positive for pain) in relation to the total quantity of false positives and true negatives (e.g., input data representing a disc that is not painful is correctly classified as negative for pain). The FPR may also be represented as "1—specificity."

A two-dimensional ROC space may be defined using FPR on the x-axis and TPR on the y-axis. Thus, each implementation of each model being evaluated may be represented by one point in ROC space based on the FPR and TPR for the classifier. A model with perfect recall would yield a point in the upper left corner (coordinate (0,1)) of the ROC space, representing 100% sensitivity (no false negatives) and 100% specificity (no false positives). In some embodiments, a model may be evaluated using different thresholds for its final classification output score. The points for different thresholds of a given model may be connected to form a curve. Classifiers with larger areas under their ROC curve (AUC) may generally be considered to produce more accurate results than those with smaller AUCs. The specific threshold to be used for a given classifier may be selected based on a preference for maximizing TPR, minimizing FPR, or striking a balance therebetween.

In some embodiments, the training system 200 (or individual components thereof) for training an ML model to evaluate MRS spectrum data and assess pain in intervertebral discs or other ROIs may be implemented on one or more host devices, such as blade servers, midrange computing devices, mainframe computers, desktop computers, or any other computing device configured to provide computing services and resources. For example, a single host device or set of host devices may include data stores for MRS acquisition data 202, processed spectrum data 204, ground truth diagnostic data 206, ground truth outcome data 208, and training data 212. The same or a different host device or set of host devices may execute a signal processor 110, training data generator 210, model trainer 220, or some combination thereof. One example of a training system computing device 800 on which the training system 200 may be implemented is shown in FIG. 8. The training system 200 may include any number of such computing devices.

In some embodiments, the features and services provided by the training system 200 may be implemented as web services consumable via one or more communication networks. In further embodiments, the training system 200 (or individual components thereof) is provided by one or more virtual machines implemented in a hosted computing environment. The hosted computing environment may be a cloud computing environment and may include one or more rapidly provisioned and released computing resources, such as computing devices, networking devices, and/or storage devices.

ML Model Training for Acquisition Data Evaluation

Figure 3:
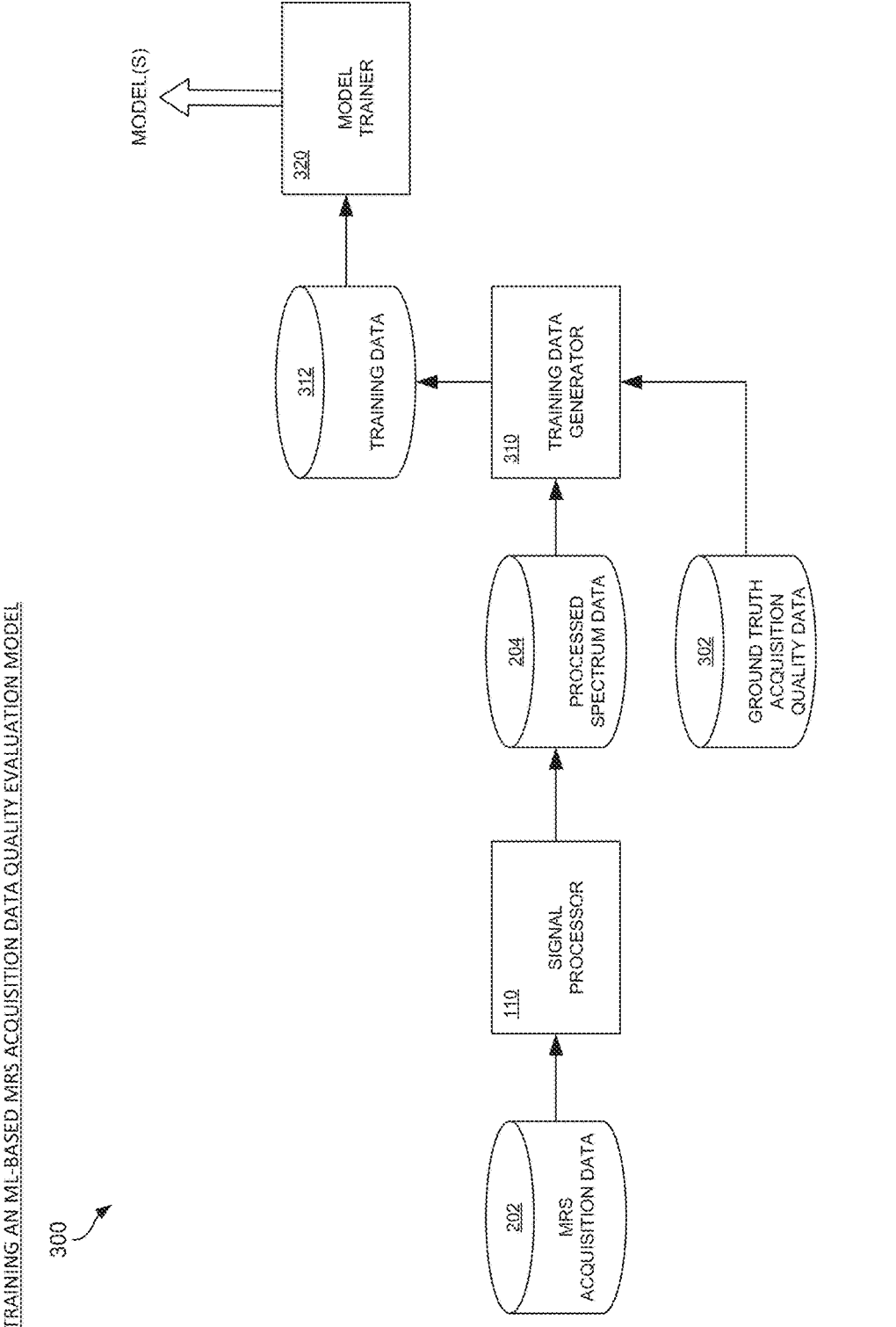
FIG. 3 is a block diagram illustrating data flows and interactions of various computing components to train a machine learning based system for evaluating magnetic resonance spectroscopy data quality according to some embodiments.

With reference to an illustrative embodiment, FIG. 3 shows an example process for training an ML model to evaluate the quality of acquisition data prior to—or in combination with—using the data to assess ROIs. Advantageously, one or more ML models may be trained to classify raw and/or processed acquisition data as having one or more properties indicative of "technical failures" other indications of low-quality MRS data acquisition. In some embodiments, detection of such conditions may trigger a re-scan or other remedial action that can be performed while a patient is still available, rather than being manually detected afterwards and resulting in a lost opportunity to assess disc pain.

In some embodiments, indicators of low-quality MRS data acquisition may include excessive endplate lipids (e.g., from poor voxel positioning), low SNR, poor shim (from the MRI scanner), and/or spectral artifacts. Note that endplate lipids are distinct from lipids intrinsic to the disc being scanned. Excessive endplate lipids may be an indirect indicator of poor voxel prescription. For example, the voxel may not be positioned within the disc, but rather includes a nearby anatomical structure such as a vertebral body (bone). This type of poor voxel prescription may be caused by patient movement (the voxel is no longer at same the position in the patient's body at is originally was when the "localizer" was run), poor positioning of the voxel to begin with by the MRS system technician, or difficulty in voxel positioning due to poor MRS system user interface design Training data may be obtained by performing MRS procedures on patient ROIs, and labeling the resulting MRS spectrum data as having one or more properties indicative of low-quality acquisition data. Illustratively, the training data may include, for individual discs or other ROIs, a pair of training data items including a training data input item (e.g., a feature vector) and a corresponding reference data output item (e.g., a reference data output vector) mapped to the training data input item. The reference data output item may include data that indicates, for the training data input item, a classification result of high quality/low quality, or a set of classification results for each of a plurality of indications of a low-quality acquisition (collectively referred to herein as "low-quality acquisition indicators").

FIG. 3 illustrates a set of input MRS acquisition data 202 generated from performing MRI procedures on patients. The MRS acquisition data 202 may be processed by the signal processor 110 to generate processed spectrum data 204, as described herein. Ground truth acquisition quality data 302 may include data regarding results of one or more evaluations of the MRS acquisition data 202 and/or processed spectrum data 204. For example, MRS acquisition data 202 and/or processed spectrum data 204 may be manually evaluated to detect the presence of one or more low-quality acquisition indicators for purposes of assessing disc pain, such as excessive lipids, low SNR, and/or spectral artifacts. Examples of detecting low-quality acquisition indicators are described in greater detail in U.S. Patent Application Publication No. 2019/030739.

The ground truth acquisition quality data 302 may indicate whether any low-quality acquisition indicator is detected for a particular item of processed spectrum data 204, and/or which specific low-quality acquisition indicators are detected. For example, an item of ground truth acquisition quality data 302 may include separate classification labels for each of a plurality of low-quality acquisition indicators, such as one label providing a binary classification as positive or negative for excessive lipid, one label providing a binary classification as positive or negative for low SNR, and one label providing a binary classification as positive or negative for spectral artifacts. The example low-quality acquisition indicators described herein are illustrative only, and are not intended to be limiting, required, or exhaustive. In some embodiments additional, fewer, and/or alternative low-quality acquisition indicators may be considered.

A training data generator 310 may generate a corpus of training data for training one or more models. The specific format of training data may depend on the particular type of model being trained. Illustratively, the corpus of training data may include a pair of a training data input item and a corresponding reference data output item for each disc that is part of the training set.

In some embodiments, a training data input item may be a feature vector composed of multiple elements, where individual elements represent the values of individual bins of processed spectrum data 204, as described in greater detail herein. An example routine for generating a feature vector to represent processed spectrum data 204 for a particular disc is shown in FIG. 5. In some embodiments, raw MRS acquisition data 202, or MRS acquisition data 202 that has undergone different combinations of processing, may be used to generate training data instead of—or in addition to—processed spectrum data 204. For example, raw MRS acquisition data 202 may undergo signal conditioning, frequency correction, and phase correction, and the result (with or without performing frame editing) may be used to generate training data input vectors composed of elements that correspond to values extracted from the data. The example combinations of processing that may be applied to MRS acquisition data 202 to generate training data as described herein are illustrative only, and are not intended to be limiting, required, or exhaustive. In some embodiments, other combinations of processing operations may be performed, such as any combination or sequence of operations described with respect to the signal processor 110 subsystems shown in FIG. 1B.

For each training data input item, a corresponding reference data output item may indicate whether the corresponding MRS spectrum data has one or more low-quality acquisition indicators for purposes of assessing disc pain. For example, the reference data output item may be a binary value, where 1 represents positive for any property indicating low quality, and 0 represents negative for any property indicating low quality. As another example, the reference data output item may be an n-dimensional vector in which each element is a binary value indicating the presence or absence of a corresponding low-quality acquisition indicator of the n low-quality acquisition indicators that the model is to be trained to detect (e.g., where the n properties include excessive lipids, low SNR, spectral artifacts, other properties, or some subset thereof).

In some embodiments, the training data generator 310 may reserve a portion of the training data pairs to be used to test the trained model(s). For example, the training data generator 310 may have access to MRS spectrum data and corresponding ground truth data for n discs. The training data generator 210 may reserve a portion of the pairs (e.g., n/4 or n/10) for implementation of cross validation, as described herein. The reserved portion may in some cases be used during training in addition to validation.

The model trainer 320 may use training data 312 generated by the training data generator 310 to train one or more models. The specific algorithm for training depends on the particular type of model being trained. In one embodiment, the model trainer 320 may train an SVM to classify binned MRS spectrum data, represented by feature vector, as positive or negative for one or more low-quality acquisition indicators. In another embodiment, the model trainer 320 may train a neural network to classify binned MRS spectrum data, represented by feature vector, as positive or negative for one or more low-quality acquisition indicators.

The example models and training routines described herein are illustrative only, and are not intended to be limiting, required, or exhaustive. In some embodiments, other models may be used instead of the neural network and SVM-based models described above. For example, the model trainer 320 may train a Bayesian classifier, a linear regression model, or logistic regression model to classify binned MRS spectrum data as either positive or negative for one or more properties indicating low-quality data.

In some embodiments, an ensemble technique may be employed in which multiple algorithms or models are used, as described herein. In some embodiments, an ROC curve may be used to evaluate the performance of a model or ensemble. Based at least partly on the ROC curve, the best performing model or ensemble may be deployed for use.

In some embodiments, a training system 300 (or individual components thereof) for training an ML model to detect low-quality acquisition indicators may be implemented on one or more host devices, such as blade servers, midrange computing devices, mainframe computers, desktop computers, or any other computing device configured to provide computing services and resources. For example, a single host device or set of host devices may include data stores for MRS acquisition data 202, processed spectrum data 204, ground truth acquisition quality data 302, and training data 312. The same or a different host device or set of host devices may execute a signal processor 110, training data generator 310, model trainer 320, or some combination thereof. One example of a training system computing device 800 on which the training system 300 may be implemented is shown in FIG. 8. The training system 300 may include any number of such computing devices.

In some embodiments, the features and services provided by the training system 300 may be implemented as web services consumable via one or more communication networks. In further embodiments, the training system 300 (or individual components thereof) is provided by one or more virtual machines implemented in a hosted computing environment. The hosted computing environment may be a cloud computing environment and may include one or more rapidly provisioned and released computing resources, such as computing devices, networking devices, and/or storage devices.

ML Model Training Routine

FIG. 4 is a flow diagram of an illustrative routine 400 that may be executed by a training system 200 or 300 to train an ML model for evaluation of acquisition data quality or assessment of pain in an ROI. Advantageously, the routine 400 (also referred to as a computer-implemented method) may generate training data including feature vector representations of spectrum data that are standardized acquisition-to-acquisition, disc-to-disc, and patient-to-patient such that a consistent set of features can be learned. Although the routine 400 will be described with reference to training an ML using spectrum data regarding intervertebral discs, it will be appreciated that training may also or alternatively be performed using spectrum data for other ROIs.

Portions of the routine 400 will be described with further reference to the illustrative data flows and interactions between components of the training systems 200 and 300 shown in FIGS. 2 and 3. Additional portions of the routine

400 will be described with further reference to the illustrative feature vector generation routine illustrated in FIGS. 5 and 6.

The routine 400 begins at block 402. The routine 400 may begin in response to an event, such as when a training system begins operation, or in response to some other event. When the routine 400 is initiated, a set of executable program instructions stored on one or more non-transitory computer-readable media (e.g., hard drive, flash memory, removable media, etc.) may be loaded into memory (e.g., random access memory or "RAM") of a computing device, such as the training system computing device 800 shown in FIG. 8. In some embodiments, the routine 400 or portions thereof may be implemented on multiple processors or computing devices, serially or in parallel.

At block 404, the training system executing the routine 400 may obtain feature vectors representing spectrum data generated for discs. An example routine for generating feature vectors representing spectrum data is shown in FIG. 5, and an example feature vector generated from a set of spectrum data is shown in FIG. 6.

At block 406, the training system may obtain labels for the feature vectors obtained in block 404. In some embodiments, the labels may be ground truth labels indicating whether a corresponding feature vector is associated with intervertebral disc pain (e.g., ground truth diagnostic data 206) or whether a corresponding feature vector is associated with one or more low-quality acquisition indicators (e.g., ground truth acquisition quality data 302). For example, a patient may undergo a provocative discography procedure in addition to the MRS procedure by which acquisition data and subsequent spectrum data is generated. Each set of acquisition data generated for a particular disc (also referred to as a "study"), or each set of processed spectrum data generated therefrom, may be associated with provocative discography results for the particular disc. The provocative discography results serve as the ground truth for the disc during training processes to train ML models to classify processed spectrum data as indicative of pain or indicative of no pain. In addition, or alternatively, each set of processed spectrum data may be associated with results of manual identification of low-quality acquisition indicators, which serve as the ground truth for the processed spectrum data during training processes to train ML models to classify processed spectrum data as indicative of one or more classes of low-quality acquisition.

The training system may access the ground truth labels and, based thereon, label corresponding feature vectors accordingly. The labeled feature vectors may be stored as training data in a training data store.

In some embodiments, a some or all sets of processed spectrum data may not have been previously evaluated for low-quality acquisition indicators. For such sets of processed spectrum data, a training data generator 210 or 310 may generate or otherwise obtain labels for the corresponding feature vectors. For example, the training data generator 210 or 310 may provide a user interface for healthcare professionals, spectroscopists, or other experts. The user interface may be a graphical user interface delivered as a web page, mobile application interface, desktop application interface, or via some other mechanism of delivery. Users may use the interface to view processed spectrum data and indicate which sets of processed spectrum data do or do not include low-quality acquisition indicators, which low-quality acquisition indicators are present, etc. Interactions to indicate the presence or absence of low-quality acquisition indicators (or other associated information) can be used to generate ground truth data that may be associated with the feature vectors generated from the sets of processed spectrum data.

At block 408, the training system may select training data to be used during the current instance of the routine 400 to train a machine learning model. In some embodiments, the training system may separate the training data pairs (feature vectors and corresponding ground truth labels) into a training set and a testing set. The training set may be used to train the machine learning model, and the testing set may be used to test the trained machine learning model. Advantageously, using a separate testing set to test the performance of the machine learning model can help to determine whether the trained machine learning model can generalize the training to new inputs that were not presented to the machine learning model during training (or during an iteration of testing). In some embodiments, the training data may not necessarily be separated into two separate sets, but rather a subset of the training data may be selected for testing while the entirety of the set may be used for training. This configuration may be used when, for example, there is less than a threshold quantity of training data pairs available and it is desirable to use as much available training data as possible to train the model.

At block 410, the training system can initialize the machine learning model to be trained. In some embodiments, the machine learning model may be implemented as a support vector machine (SVM), and initializing the model may include determining hyperparameters of the training algorithm. In some embodiments, the machine learning model may be implemented as a neural network, and initializing the model may include configuring the quantity of layers and nodes per layer, setting weights between nodes to randomly-determined values, and the like. The example machine learning models described herein are illustrative only, and are not intended to be limiting, required, or exhaustive. In some embodiments, other machine learning models may be trained, and the models may be initialized accordingly. For example, a machine learning model may include a k-nearest neighbors model, a Bayesian classifier, or any other classification model.

At block 412, the training system can perform a training epoch using the training set. A training epoch is a pass of the entire training set by the machine learning algorithm to produce or update a model. The process of training a machine learning model may involve one or more epochs, depending upon various constraints (e.g., time, resources, etc.) and/or resulting evaluation of the model (e.g., validation). In some embodiments, large training sets may be grouped into batches, and the machine learning algorithm may iterate through batches until the training set has been completely processed. The specific manner in which the training epoch proceeds depends on the particular machine learning algorithm being used and model being trained. For example, if an SVM is being trained, then the training process may involve determining a hyperplane that optimally separates classes of training data as determined using a loss function such as a hinge loss. As another example, if a neural network is being trained, then the training process may involve performing a forward pass on each feature vector and performing backpropagation to update the parameters of the neural network based on a loss function such as a cross-entropy loss function.

At block 414 the model training system can evaluate the results of the training process. In some embodiments, the training system may evaluate the results using a validation process. For example, the training set may be separated into k folds (where k is an integer, such as 5) for k-fold cross validation. Each of the k folds may be used to test the model, producing various statistical measures of accuracy, such as precision, recall, the AUC of an ROC curve, or other statistical measures of accuracy. Models with greater degrees precision (e.g., percentage of model output data with positive classifications that are correct) and recall (e.g., percentage of ground truth positive classifications identified correctly in model output data) may generally considered to produce more accurate results than those with lower degrees of precision or recall. Models with larger areas under their ROC curve (AUC) may generally be considered to produce more accurate results than those with smaller AUCs, as described herein.

At decision block 416, the training system can in some embodiments determine whether one or more stopping criteria are met. For example, a stopping criterion can be based on the accuracy of the machine learning model as determined using the test set(s) in a cross-validation process. As another example, a stopping criterion can be based on the number of epochs of training that have been performed, the elapsed training time, computing resources consumed, or the like. If the one or more stopping criteria are met, the routine 400 can proceed to block 418; otherwise, the routine 400 can return to block 412 or some other prior block of the routine 400.

At block 418, the training system can store and/or distribute the trained model (e.g., by sending the trained model to a persistent data store and/or by sending the trained model to one or more diagnostic systems). For example, as shown in FIG. 8, a trained model 830 can be sent to a diagnostic system computing device 850 (or multiple diagnostic system computing devices) for use in MRS data evaluation procedures. The routine 400 may then terminate at block 420.

Example Routine for Generation of Feature Vectors

FIG. 5 is a flow diagram of an illustrative routine 500 that may be executed by a diagnostic system 100 or a training system 200 or 300 to generate feature vectors from spectrum data. Advantageously, the routine 500 (also referred to as a computer-implemented method) may be used to generate feature vectors comprising data representing a consistent sampling of the data throughout a particular range of interest, even when the spectrum data may include data points that vary in placement from acquisition-to-acquisition for a given disc, from disc-to-disc, and from patient-to-patient. For example, the data points may represent points on a coordinate system in which the x-axis represents "chemical shift" or frequency of the spectrum at the particular point, and the y-axis represents amplitude of the spectrum at the particular point. However, a first set of spectrum data may include a quantity of data points with particular x-axis values, while a second set of spectrum data generated from a second set of acquisition data may include the same quantity of data points, but with some or all of the data points having different x-axis values than some or all of the data points in the first set of spectrum data. Moreover, the points may not be evenly distributed across the spectrum such that the quantity of points with a particular frequency band of interest may not be consistent from one set of spectrum data to another. By performing routine 500, a diagnostic system 100 or a training system 200 or 300 can generate feature vectors from spectrum data that represent a consistent sampling of the spectrum, both in quantity and interval, thus providing a consistent base from which to train a machine learning model or use a trained model.

Portions of the routine 500 will be described with further reference to the illustrative spectrum data set and feature vector shown in FIG. 6.

The routine 500 begins at block 502. The routine 500 may begin in response to an event, such as when a training system or diagnostic system begins operation, or in response to some other event. When the routine 500 is initiated, a set of executable program instructions stored on one or more non-transitory computer-readable media (e.g., hard drive, flash memory, removable media, etc.) may be loaded into memory (e.g., random access memory or "RAM") of a computing device, such as the training system computing device 800 or diagnostic system computing device 850 shown in FIG. 8. In some embodiments, the routine 500 or portions thereof may be implemented on multiple processors or computing devices, serially or in parallel.

At block 504, the system executing the routine 500 (a diagnostic system 100 or a training system 200 or 300) may obtain spectrum data for a region of interest, such as an intervertebral disc. For example, spectrum data may be obtained for use in generating a feature vector for training of a machine learning model, such as a model for detecting low-quality acquisition indicators or for assessing disc pain. As another example, spectrum data may be obtained at inference time for evaluation using a trained machine learning model. Advantageously, in some embodiments the same or substantially the same operations may be performed to generate feature vectors for training and inference, ensuring consistency of the sampling and overall representation of the spectrum data for evaluation across acquisitions, discs, and patients.

FIG. 6 illustrates processed spectrum data 600 obtained for a particular region of interest, such as an intervertebral disc of a patient. The processed spectrum data 600 may be obtained in the form of quantity of data points representing amplitudes of the spectrum at particular frequencies or "chemical shifts." As shown, the points may be visualized as a graph in which the x-axis represents chemical sift and the y-axis represents amplitude of the spectrum. Although spectrum data may represent a relatively large initial range of chemical shifts (e.g., 10.0 to 0.0), only a portion of that range may be of interest for evaluation using the machine learning models as described herein. The chemical shift range of interest 602 (also referred to as the frequency band of interest) may extend between a lower chemical shift range boundary (also referred to as a lower frequency band boundary) to an upper chemical shift range boundary (also referred to as an upper frequency band boundary). The system executing the routine 500 may extract only the data points within the chemical shift range of interest 602 for use in subsequent blocks of the routine.

In some embodiments, the lower chemical shift range boundary and upper chemical shift boundaries may be set to define a chemical shift range of about 0.0 to about 4.1, about 0.2 to about 4.0, or about 0.4 to about 3.9. Illustratively, these boundaries may correspond to chemical shift values for PA at or near the lower chemical shift boundary to CA at or near the upper chemical shift range boundary within the spectrum. Example spectra and chemical shifts of particular chemicals are discussed in "Magnetic Resonance Spectroscopy (MRS) Can Identify Painful Lumbar Discs and May Facilitate Improved Clinical Outcomes of Lumbar Surgeries for Discogenic Pain," by Gornet et al. published in the European Spine Journal (2019) 28:674-687, which is incorporated by reference herein and made part of this specification.

At block 506, the system executing routine 500 may segment the values in the chemical shift range of interest into bins. The values may be binned to account for the variability in spectrum data extracted within the chemical shift range of interest. In some embodiments, the data points may not necessarily be evenly distributed across the initial range of chemical shifts. This can result in a variable quantity of data points being present within the chemical shift range of interest from set-to-set of processed spectrum data. In addition, or alternatively, this can result in a variable distribution across the chemical shift range of interest from set-to-set of processed spectrum data. In order to ensure that feature vectors provide a consistent representation of data within the chemical shift range of interest from set-to-set of processed spectrum data, the points may be binned according to predetermined binning parameters that remain consistent for each feature vector. In some embodiments, the binning parameters may include the size of feature vector to be generated and the size of the chemical shift range of interest.

A feature vector may be an n-dimensional vector, wherein n is an integer that remains constant for each feature vector. In general, n may be any positive integer, such as 8, 10, 12, 20, 25, 50, 64, 100, 128, 200, 256, 500, 512, 1000, 1024, 2048, or more. Therefore, to bin the data points in the chemical shift range of interest, the data points may be separated into n different bins. To ensure consistent representation of spectrum data from feature vector to feature vector, each bin may be defined for a particular subrange of the chemical shift range of interest. For example, the size of the chemical shift range of interest may be divided by the quantity of feature vector dimensions to determine the size of the subregion of the chemical shift range of interest for each bin. In the example illustrated in FIG. 6, the size of the chemical shift range of interest is 4.1 (4.1–0.0=4.1), the quantity of feature vector dimensions is 64, and the size of the chemical shift range of interest for each bin is 0.0640625. Thus, there would be 64 bins for 64 subranges of the chemical shift range of interest, each subrange being of size 0.0640625, beginning with bin index 0 at chemical shift 0.0, and ending with bin index 63 that extends to chemical shift 4.1. For simplicity of illustration, only 8 bins are shown in the binned data points 610. However, in this example each of the eight bins would be separated into 8 more bins, resulting in 64 bins.

To segment data points into the bins, the system executing the routine 500 may iterate through the data points and add the amplitude value (e.g., the y value) of each data point to the bin with a range encompassing the chemical shift value (e.g., the x value). Due to the variability in sets of processed spectrum data from which data points are extracted, some bins may have a different quantity of amplitude values corresponding to a different quantity of data points than other bins within the same set of binned data points 610. For example, bin 612 is illustrated as spanning a range of chemical shift values that encompasses 8 data points, while bin 614 is illustrated as spanning a range of chemical shift values encompassing 10 data points. In some cases, one or more bins may be associated with ranges of chemical shift values that do not encompass any data points extracted from the processed spectrum data 600.

At decision block 508, the system executing the routine 500 may identify the bins (if any) that include multiple amplitude values. If there are any such bins, the routine 500 may proceed to block 510. Otherwise, if there are no such bins, the routine 500 may proceed to decision block 512.

At block 510, the system executing the routine 500 may generate, for each bin having multiple amplitude values, a corresponding single value for the bin that is representative of the multiple amplitude values. This value may therefore be a representative value for the subrange of the chemical shift range of interest the corresponds to the bin. In some embodiments, the single value may be a mean of the amplitude values. In some embodiments, the single value may be a median or mode of the amplitude values. In some embodiments, other functions may be evaluated to determine a single value representative of all amplitude values of a bin.

At decision block 512, the system executing the routine 500 may identify the bins (if any) that include no amplitude values. If there are any such bins, the routine 500 may proceed to block 514. Otherwise, if there are no such bins, the routine 500 may proceed to decision block 516.

At block 514, the system executing the routine 500 may generate, for each bin having no amplitude values, a representative value for the subrange of the chemical shift range of interest associated with the bin. In some embodiments, the value for a bin having no amplitude values may be interpolated from the values of surrounding bins. For example, linear interpolation may be used in which one bin (e.g., a bin with index 10) may have zero values, while the bin immediately preceding the bin in the chemical shift range of interest (e.g., a bin with index 9) and the bin immediately following the bin in the chemical shift range of interest (e.g., a bin with an index of 11) may each have values, such as 0.8 and 0.6, respectively. To interpolate the value for the bin with index 10, the system may determine the mean of the values of bins with indices 9 and 11. In this example, the value assigned to the bin with index 10 may be 0.7. In some embodiments, other methods of interpolation may be used that consider more than just the preceding and following bins in the chemical shift range of interest. For example, polynomial interpolation may be derived in which a polynomial function that goes through 3 or more points may be derived, and then the values of additional bins may be determined using the derived polynomial function. If there are n bins with values, there is exactly one polynomial of degree at most n−1 going through all the values. In some embodiments, other functions may be evaluated to determine values for bins without amplitude values from data points.

At block 516, the system executing the routine 500 can normalize the values across all bins to produce a final feature vector for a given set of processed spectrum data. In some embodiments, normalization may involve dividing each value preliminarily determined according to prior blocks of the routine 500 by the maximum of all such values. As a result, the normalized values of each bin will fall in the range 0.0-1.0, with the bin having the maximum value being normalized to a value of 1.0.

FIG. 6 shows a feature vector 620 generated from the set of processed spectrum data 600. The graphic illustration of the feature vector 620 uses the x-axis to represent the index of each particular value within the feature vector, and the y-axis to represent the normalized value at each index. The indices correspond to the bins generated as described herein. The graphic illustration further shows the results of interpolation, with a full curve being shown to provide a value for each of the 64 bins.

At decision block 518, the system executing the routine 500 can determine whether there are additional sets of processed spectrum data (e.g., for additional discs) from which feature vectors are to be derived. If so, the routine 500 may return to block 504 as needed. Otherwise, the routine 500 may terminate at block 520.

In some embodiments, generation of the feature vector may further involve recognizing regions along the spectrum generally associated with certain specific biomarker chemicals of diagnostic interest (e.g., spectral regions of diagnostic interest or "SRDI"), and extracting target data from such SRDIs. These SRDI's will typically have known ranges, with upper and lower bounds, along the x-axis of the spectrum, and thus making up their own bins that are defined for respective data extraction. In some cases, such bins may provide only an ability to find a certain feature of the spectrum (e.g., a regional "peak"), and this information can then be used to determine and extract other information (e.g., power under a peak region, which may be determined to include spectral power around the peak that extends outside of the respective "bin"). Furthermore, certain artifacts may cause chemical shift error in the spectra despite corrections provided in the signal processing. The data extractor 121 may recognize a certain feature in one respective SRDI bin (e.g., PG peak), and then adjust the location for another target SRDI from where it might otherwise be sought (e.g., based upon a prescribed distance from the first recognized target peak, vs. fixed relative locations for the SRDIs along the x-axis). In some embodiments, to compensate for slight shifts in the spectrum (e.g., chemical shift errors) after a regional peak is identified in a specified bin, the bin and/or the spectrum can be shifted to align the regional peak with the center of the bin, and an area under the curve can be taken for a region (e.g., in the shifted bin) centered on the located regional peak.

In some embodiments, in addition to representative values for subregions of a chemical shift region of interest, a feature vector may include: a first element for a measurement of a degree of PG in the corresponding MRS spectrum data 204 for a particular disc, as represented by a peak within a particular bin associated with PG; a second element for a measurement of a degree of LA in the corresponding MRS spectrum data 204 for the disc, as represented by a peak within a particular bin associated with LA; a third element for a measurement of a degree of AL in the corresponding MRS spectrum data 204 for the disc, as represented by a peak within a particular bin associated with AL; one or more other elements (e.g., measurements of PG, CA, etc.); or some other subset or combination thereof.

In some embodiments, a generated feature vector may include one or more data items in addition to those representing or derived from processed MRS spectrum data. For example, data regarding patient characteristics may be included, such as values representing one or more of: height, weight, body mass index (BMI), age, gender, race, comorbidities (e.g., other ailments, treatment, surgeries such as hip or knee replacement, spinal fusion, etc.), smoking status, alcohol/drug use status, diagnosis of systemic inflammation such as neuralgia, other patient characteristics, or some combination thereof. As another example, information regarding disc characteristics other than MRS spectrum data may be included, such as values representing one or more of: disc height, degree of hydration of the disc, other properties determined through MRI or MRS, identified anatomic level of the disc (e.g., L1-L2 disc), presence or absence of herniations, annular tears, or adjacent Modic end-plate changes, feature vectors or other representations of MRS spectrum data for other discs of same patient (e.g., to effectively normalize input across discs for a particular patient), other disc properties, or combinations thereof.

Example Routine for Evaluation of MRS Data and Assessment of Pain

Figure 7:
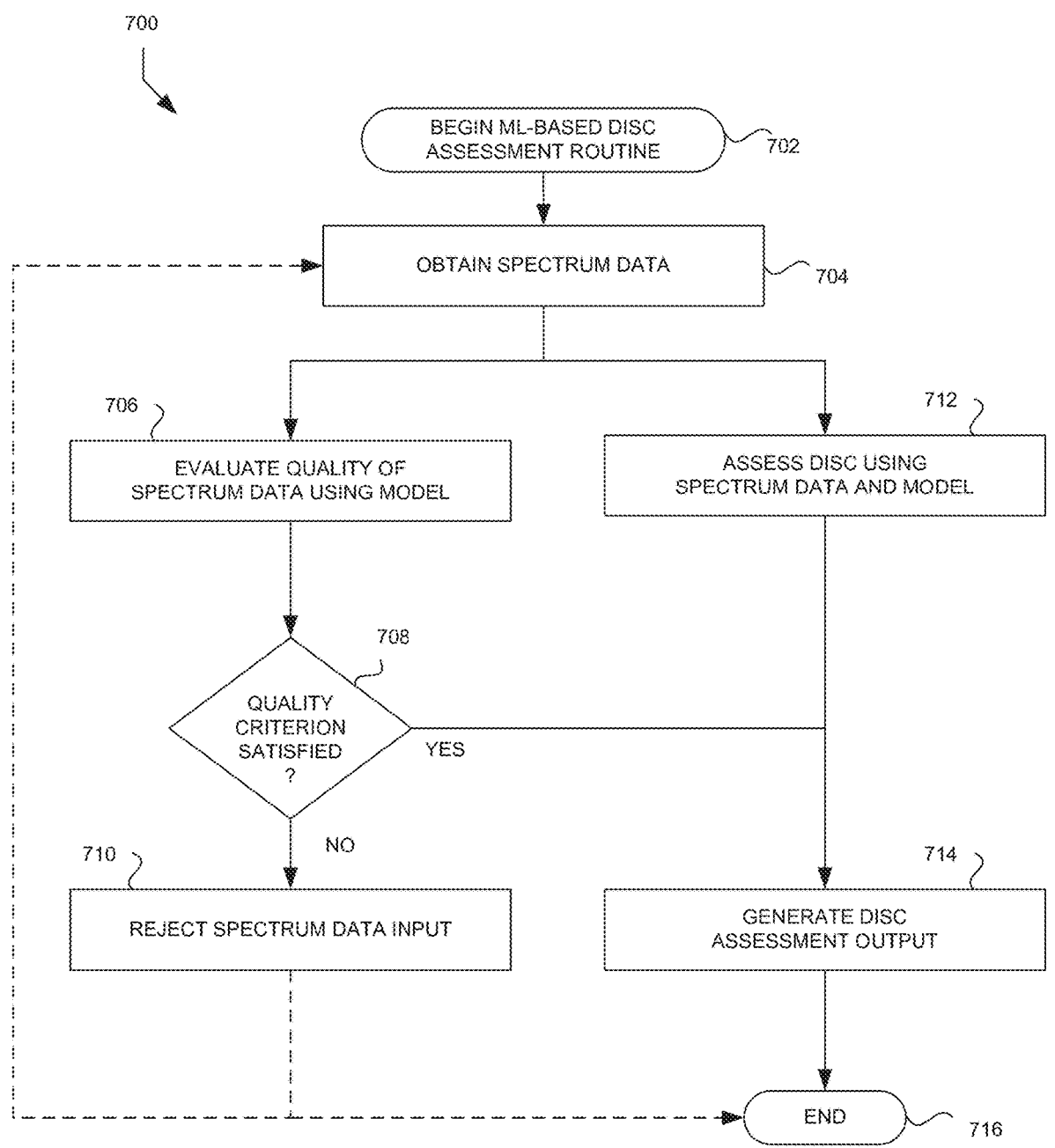
FIG. 7 is a flow diagram of an illustrative routine performed by a machine learning-based disc assessment system to evaluate the quality of input data and/or assess a medical condition associated with a region of interest according to some embodiments.

FIG. 7 is a flow diagram of an illustrative routine 700 (also referred to as a computer-implemented method) that may be executed by a diagnostic system 100 or a component thereof (e.g., an ML model-based diagnostic processor 120) to evaluate the quality of input data and/or assess disc pain based on the input data.

The routine 700 begins at block 702. The routine 700 may begin in response to an event, such as when the diagnostic system begins operation. When the routine 700 is initiated, a set of executable program instructions stored on one or more non-transitory computer-readable media (e.g., hard drive, flash memory, removable media, etc.) may be loaded into memory (e.g., random access memory or "RAM") of a computing device and executed by a computer processor. In some embodiments, the routine 700 or portions thereof may be implemented on multiple processors, serially or in parallel.

At block 704, the ML model-based diagnostic processor 120 or some other module or component may receive MRS spectrum data for a patient's disc (referred to in the description that follows as the "current disc"). For example, the ML model-based diagnostic processor 120 may receive raw MRS spectrum data, partially-processed MRS spectrum data, and/or processed MRS spectrum data generated from an MRS procedure on a patient with a voxel positioned on the current disc. Processing applied to the MRS spectrum data may include signal conditioning, frequency correction, phase correction, frame editing, other processes, or some combination thereof.

At block 706, the ML model-based diagnostic processor 120 or some other module or component may evaluate the input MRS spectrum data. In some embodiments, evaluation may be performed using one or more ML models trained as described herein to produce classification output indicating whether the input MRS spectrum data has one or more low-quality acquisition indicators of being low quality for purposes of assessing disc pain. For example, the ML model-based diagnostic processor 120 may generate a feature vector as described herein, and then process the feature vector using an ML model trained to produce classification results indicative of pain in a ROI as described herein.

At decision block 708, the ML model-based diagnostic processor 120 or some other module or component may determine whether evaluation of the MRS spectrum data satisfies a quality criterion. The quality criterion may be based on the classification output generated at block 706. For example, if the classification output indicates the presence of one or more low-quality acquisition indicators (e.g., a positive classification for any low-quality acquisition indicators, or an overall classification of the MRS spectrum data as being indicative of a low-quality acquisition), the routine 700 may proceed to block 710 where the input is rejected. New/replacement MRS spectrum data may then be obtained at block 704, or the routine 700 may terminate at block 716.

At block 712, the ML model-based diagnostic processor 120 or some other module or component may assess the current disc using the input MRS spectrum data. Assessment may be performed using one or more ML models trained as described herein to produce classification output indicating whether the input MRS spectrum data is indicative of a painful disc (e.g., a positive classification for pain) or not indicative of a painful disc (e.g., a negative classification for pain). For example, the ML model-based diagnostic processor 120 may generate a feature vector as described herein, and then process the feature vector using an ML model trained to produce classification results indicative of pain in a ROI as described herein. In some embodiments, the feature vector may be the same feature vector as used in block 706 (or a copy thereof), or it may be a different feature vector that includes additional or alternative data (e.g., measurements of PG, CA, patient body mass index (BMI), etc.).

At block 714, the ML model-based diagnostic processor 120 or some other module or component may generate output of the assessment performed at block 512. In some embodiments, the output may be a report and/or on-screen display indicating whether the current disc is painful, a probability or other degree of confidence in classification of whether the current disc is painful, the presence or absence of any low-quality acquisition indicators, other information, or any combination thereof.

Although blocks 706 and 712 are shown as being performed in parallel, and block 714 is shown as being performed after blocks 712 and 708, the example is provided for purposes of illustration only and is not intended to be limiting, required, or exhaustive. In some embodiments, a determination of whether a quality criterion is satisfied at decision block 708 may be made before assessment of the disc for disc pain, and therefore performance of the operations of block 712 may not occur if the quality criterion is not satisfied. In some embodiments, the operations of block 712 are performed prior to the operations of block 706.

At block 716 the routine 700 may terminate.

In some embodiments, after generation of the disc assessment output, a proposed treatment may be determined. For example, a health care professional may determine whether to recommend a surgical procedure, physical therapy, regenerative cell therapy (or other forms of injectable biologics or other therapeutic injectables), or other therapies based on the disc assessment output.

In some embodiments, as shown in FIG. 8, operational data 840 regarding performance the routine 700 may be provided to a training system or some other system. For example, classification output regarding low-quality acquisition indicators, classification output regarding whether the spectrum data is indicative pain, feature vectors generated during the routine, spectrum data input and processed during the routine, treatment data regarding treatments recommended or administered, outcome data regarding short and/or long-term outputs from the treatments (or absence of treatments), other data, or any combination thereof may be provided to a training system as operational data 840. The training system may then use the operational data 840 to generate training data and/or validation data for retraining of one or more models using additional iterations of ML model training procedures such as those described herein. In this way, the ML models used by the ML model-based diagnostic processor 120 may be continuously or periodically updated.

In some embodiments, outcome data regarding outcomes of treatment (or omission of treatment for a period of time) may be provided to a training system or some other system. For example, clinically-determined outcome data such as ODI or VAS scores may be provided by a healthcare provider to the training system or to an ingestion system from which training data to retrain one or more ML models may be obtained. As another example, patients may self-report outcomes, either through patient-controlled devices or applications (e.g., mobile applications, web sites, etc.) or through healthcare providers. Patients may indicate which treatment was applied, or the treatment may be provided by a healthcare provider and later linked to patient-provided outcome data. Patients may indicate whether pain has been reduced or eliminated as a binary determination (yes/no), or on a scale akin to the VAS or ODI. Patients may self-report outcomes at some reasonable time interval after the procedure (e.g., around 3 to 6 months, or at predetermined or dynamically determined timeframes between about 1 to 24 months after treatment). The training system may then use the outcome data to generate ground truth outcome data for retraining of one or more models using additional iterations of ML model training procedures such as those described herein. In this way, the ML models used by the ML model-based diagnostic processor 120 may be continuously or periodically updated.

Example Computing Systems

FIG. 8 illustrates various components of an example training system computing device 800 configured to implement various ML training functionality, such as the functionality of the training data generator 210, model trainer 220, training data generator 310, and/or model trainer 320.

In some embodiments, as shown, the training system computing device 800 may include: one or more computer processors 802, such as physical central processing units (CPUs); one or more network interfaces 804, such as a network interface cards (NICs); one or more computer readable medium drives 806, such as a high density disk (HDDs), solid state drives (SSDs), flash drives, and/or other persistent non-transitory computer-readable media; and one or more computer-readable memories 810, such as random access memory (RAM) and/or other volatile non-transitory computer-readable media.

The computer-readable memory 810 may include specific instructions (e.g., computer program instructions) that one or more computer processors 802 execute in order to implement one or more embodiments. The computer-readable memory 810 can store an operating system 812 that provides computer program instructions for use by the computer processor(s) 802 in the general administration and operation of the training system computing device 800.

In some embodiments, the computer-readable memory 810 can further include computer program instructions and other information for implementing aspects of the present disclosure. For example, the computer-readable memory 810 may include training data generation instructions 814 for managing generation of training data, such as training data 212 or 312. As another example, the computer-readable memory 810 may include model training instructions 816 for performing the functions of model trainer 220 and/or model trainer 320 to train one or more models as described herein.

FIG. 8 also illustrates various components of an example diagnostic system computing device 850 configured to implement various functionality of the diagnostic system 100.

In some embodiments, as shown, the diagnostic system computing device 850 may include: one or more computer processors 802, such as physical central processing units (CPUs); one or more network interfaces 804, such as a network interface cards (NICs); one or more computer readable medium drives 806, such as a high density disk (HDDs), solid state drives (SSDs), flash drives, and/or other persistent non-transitory computer-readable media; and one or more computer-readable memories 810, such as random access memory (RAM) and/or other volatile non-transitory computer-readable media.

The computer-readable memory 810 may include specific instructions (e.g., computer program instructions) that one or more computer processors 802 execute in order to implement one or more embodiments. The computer-readable memory 810 can store an operating system 812 that provides computer program instructions for use by the computer processor(s) 802 in the general administration and operation of the diagnostic system computing device 850.

In some embodiments, the computer-readable memory 810 can further include computer program instructions and other information for implementing aspects of the present disclosure. For example, the computer-readable memory 810 may include signal processing instructions 852 for managing the signal processing operations of the signal processor 110. As another example, the computer-readable memory 810 may include diagnostic processing instructions 854 for performing the functions of the ML model-based diagnostic processor 120 using one or more machine learning models 830 as described herein.

Terminology and Additional Considerations

All of the methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions, or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid-state memory chips or magnetic disks, into a different state. In some embodiments, the computer system may be a cloud-based computing system whose processing resources are shared by multiple distinct business entities or other users.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware, or combinations of electronic hardware and computer software. To clearly illustrate this interchangeability, various illustrative components, blocks, modules, and steps have been described above generally in terms of their functionality. Whether such functionality is implemented as hardware, or as software that runs on hardware, depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others.

What is claimed is:

1. A computer-implemented method for providing diagnostic information for a medical condition associated with a region of interest (ROI) in a patient, the computer-implemented method comprising:

obtaining, by a diagnostic system comprising computer-readable memory and one or more computer processors, processed MRS spectrum data representing output of a magnetic resonance spectroscopy (MRS) system, wherein the output of the MRS system comprises MRS acquisition data for a voxel located within the ROI;

extracting, by the diagnostic system, a subset of the processed MRS spectrum data corresponding to a chemical shift range of interest ranging from a lower chemical shift range boundary to an upper chemical shift range boundary, wherein the subset of the processed MRS spectrum data comprises a plurality of data points, and wherein a data point of the plurality of data points represents an amplitude value associated with a chemical shift value within the chemical shift range of interest;

generating, by the diagnostic system, a feature vector comprising at least eight (8) dimensions, wherein each dimension comprises a representative value for a plurality of amplitude values in a different one of a plurality of subranges of the chemical shift range of interest;

processing, by the diagnostic system, the feature vector using an ML model trained to determine, from the representative values for each of the plurality of subranges, a classification regarding the medical condition associated with the ROI; and generating, by the diagnostic system, the diagnostic information for the medical condition using the classification.

2. The computer-implemented method of claim 1, further comprising:

segmenting, by the diagnostic system, the plurality of data points into a plurality of bins, wherein after segmentation of the plurality of data points, a first bin of the plurality of bins comprises two or more data points associated with a first subrange of the plurality of subranges of the chemical shift range of interest; and generating, by the diagnostic system, a representative value for the first subrange based on a mean of the two or more data points.

3. The computer-implemented method of claim 1, further comprising:

segmenting, by the diagnostic system, the plurality of data points into a plurality of bins, wherein after segmentation of the plurality of data points, a first bin of the plurality of bins does not include any data points, and wherein the first bin is associated with a first subrange of the plurality of subranges of the chemical shift range of interest; and generating, by the diagnostic system, a representative value for the first subrange based on an interpolation from representative values of a second subrange and a third subrange of the plurality of subranges of the chemical shift range of interest.

4. The computer-implemented method of claim 1, further comprising:

determining, by the diagnostic system, one or more binning parameters; and segmenting, by the diagnostic system, the plurality of data points into a plurality of bins, wherein a quantity of bins in the plurality of bins is based at least in part on the one or more binning parameters, wherein after segmentation of the plurality of data points, a first bin of the plurality of bins comprises a data point associated with a first subrange of the plurality of subranges of the chemical shift range of interest, and wherein a size of the first subrange is based at least in part on the one or more binning parameters.

5. The computer-implemented method of claim 4, wherein determining the one or more binning parameters comprises determining a size of the feature vector and a size of the chemical shift range of interest.

6. The computer-implemented method of claim 1, further comprising processing, by the diagnostic system, the feature vector using a second ML model trained to determine, from the representative values for each of the plurality of subranges, a second classification regarding detection of a low-quality acquisition indicator, wherein the low-quality acquisition indicator comprises an indication of at least one of: excessive lipids, low signal-to-noise ratio, or spectral artifacts.

7. The computer-implemented method of claim 6, further comprising determining, by the diagnostic system based on the second classification being negative for detection of a low-quality acquisition indicator, to process the feature vector using the ML model.

8. The computer-implemented method of claim 6, further comprising determining, by the diagnostic system and based on the second classification being positive for detection of a low-quality acquisition indicator, that the MRS acquisition data is to be rejected.

9. The computer-implemented method of claim 1, wherein processing the feature vector using the ML model comprises processing the feature vector using one of: a support vector machine, a neural network, a k-nearest neighbors model, or a Bayesian classifier.

10. The computer-implemented method of claim 1, further comprising:

determining, by the diagnostic system, a value of the lower chemical shift range boundary based at least in part on a lower end of a range of chemical shift values associated with propionic acid (PA); and determining, by the diagnostic system, a value of the upper chemical shift range boundary based at least in part on an upper end of a range of chemical shift value associated with carbohydrate (CA).

11. The computer-implemented method of claim 1, further comprising determining, by the diagnostic system, a value of the lower chemical shift range boundary as 0.0, and a value of the upper chemical shift range boundary as 4.1.

12. A system for providing diagnostic information for a medical condition associated with a region of interest (ROI) in a patient, the system comprising:

computer-readable memory storing executable instructions; and one or more computer processors in communication with the computer-readable memory and programmed by the executable instructions to:

obtain processed MRS spectrum data representing output of a magnetic resonance spectroscopy (MRS) system, wherein the output of the MRS system comprises MRS acquisition data for a voxel located within the ROI;

extract a subset of the processed MRS spectrum data corresponding to a chemical shift range of interest ranging from a lower chemical shift range boundary to an upper chemical shift range boundary, wherein the subset of the processed MRS spectrum data comprises a plurality of data points, and wherein a data point of the plurality of data points represents an amplitude value associated with a chemical shift value within the chemical shift range of interest;

generate a feature vector comprising at least eight (8) dimensions, wherein each dimension comprises a representative value for a plurality of amplitude values in a different one of a plurality of subranges of the chemical shift range of interest;

process the feature vector using an ML model trained to determine, from the representative values for each of the plurality of subranges, a classification regarding the medical condition associated with the ROI; and generate the diagnostic information for the medical condition using the classification.

13. The system of claim 12, wherein the one or more computer processors are further programmed by the executable instructions to:

segment the plurality of data points into a plurality of bins, wherein after segmentation of the plurality of data points, a first bin of the plurality of bins comprises two or more data points associated with a first subrange of the plurality of subranges of the chemical shift range of interest; and generate a representative value for the first subrange based on a mean of the two or more data points.

14. The system of claim 12, wherein the one or more computer processors are further programmed by the executable instructions to:

segment the plurality of data points into a plurality of bins, wherein after segmentation of the plurality of data points, a first bin of the plurality of bins does not include any data points, and wherein the first bin is associated with a first subrange of the plurality of subranges of the chemical shift range of interest; and generate a representative value for the first subrange based on an interpolation from representative values of a second subrange and a third subrange of the plurality of subranges of the chemical shift range of interest.

15. The system of claim 12, wherein the one or more computer processors are further programmed by the executable instructions to:

determine one or more binning parameters; and segment the plurality of data points into a plurality of bins, wherein a quantity of bins in the plurality of bins is based at least in part on the one or more binning parameters, wherein after segmentation of the plurality of data points, a first bin of the plurality of bins comprises a data point associated with a first subrange of the plurality of subranges of the chemical shift range of interest, and wherein a size of the first subrange is based at least in part on the one or more binning parameters.

16. The system of claim 15, wherein to determine the one or more binning parameters, the one or more computer processors are further programmed by the executable instructions to determine a size of the feature vector and a size of the chemical shift range of interest.

17. The system of claim 12, wherein the one or more computer processors are further programmed by the executable instructions to process the feature vector using a second ML model trained to determine, from the representative values for each of the plurality of subranges, a second classification regarding detection of a low-quality acquisition indicator, wherein the low-quality acquisition indicator comprises an indication of at least one of: excessive lipids, low signal-to-noise ratio, or spectral artifacts.

18. The system of claim 17, wherein the one or more computer processors are further programmed by the executable instructions to determine, based on the second classification being negative for detection of a low-quality acquisition indicator, to process the feature vector using the ML model.

19. The system of claim 17, wherein the one or more computer processors are further programmed by the executable instructions to determine, based on the second classification being positive for detection of a low-quality acquisition indicator, that the MRS acquisition data is to be rejected.

20. The system of claim 12, wherein to process the feature vector using the ML model, the one or more computer processors are further programmed by the executable instructions to process the feature vector using one of: a support vector machine, a neural network, a k-nearest neighbors model, or a Bayesian classifier.

21. The system of claim 12, wherein the one or more computer processors are further programmed by the executable instructions to:

determine a value of the lower chemical shift range boundary based at least in part on a lower end of a range of chemical shift values associated with propionic acid (PA); and determine a value of the upper chemical shift range boundary based at least in part on an upper end of a range of chemical shift value associated with carbohydrate (CA).

22. The system of claim 12, wherein the one or more computer processors are further programmed by the executable instructions to determine a value of the lower chemical shift range boundary as 0.0, and a value of the upper chemical shift range boundary as 4.1.

* * * * *